United States Patent
Marriott

(10) Patent No.: US 9,532,983 B2
(45) Date of Patent: Jan. 3, 2017

(54) BENZOFURAN COMPOUNDS, COMPOSITIONS, KITS AND/OR METHODS THEREOF

(71) Applicant: Savannah State University, Savannah, GA (US)

(72) Inventor: Karla-Sue C. Marriott, Savannah, GA (US)

(73) Assignee: Savannah State University, Savannah, GA (US)

( * ) Notice: Subject to any disclaimer, the term of this patent is extended or adjusted under 35 U.S.C. 154(b) by 0 days.

(21) Appl. No.: 14/448,138

(22) Filed: Jul. 31, 2014

(65) Prior Publication Data

US 2015/0133498 A1    May 14, 2015

Related U.S. Application Data

(60) Provisional application No. 61/860,492, filed on Jul. 31, 2013.

(51) Int. Cl.
| | |
|---|---|
| *A61K 31/4525* | (2006.01) |
| *C07D 307/85* | (2006.01) |
| *A61K 45/06* | (2006.01) |

(52) U.S. Cl.
CPC ........... *A61K 31/4525* (2013.01); *A61K 45/06* (2013.01); *C07D 307/85* (2013.01)

(58) Field of Classification Search
None
See application file for complete search history.

(56) References Cited

FOREIGN PATENT DOCUMENTS

JP    2007-106692    *    4/2007

OTHER PUBLICATIONS

Ryoji et al (JP2007106692 (A), machine translation obtained from JPO website on Nov. 13, 2015).*
Strickley (Pharmaceutical Research, 2004; 21(2):201-230).*
Li et al (Int J Med Sci, 2012; 9(3):248-255).*
Vyas et al (Exp Op Drug Del, 2009; 6(5):499-508).*
Ruchser et al.,"The sigma-1 receptor enhances brain plasticity and functional recovery after experimental stroke", Brain, 1-15, advance of publication, (2011).
Crawford et al.,"Sigma-2 Receptor Agonists Activate a Novel Apoptotic Pathway and Potentiate Antineoplastic Drugs in Breast Tumor Cell Lines", Cancer Res., 62:313-22 (2002).
Hornick et al.,"The novel sigma-2 receptor ligand SW43 stabilizes pancreas cancer progression in combination with gemcitabine", Molecular Cancer, 9:298 (2010).

(Continued)

*Primary Examiner* — Marcos Sznaidman
*Assistant Examiner* — Rayna B Rodriguez
(74) *Attorney, Agent, or Firm* — Jordan IP Law, LLC

(57) ABSTRACT

Benzofuran compound, composition thereof, kit thereof, and/or method thereof. A benzofuran-2-carboxamide moiety may be N-arylated and/or N-alkylated, and the resulting benzofuran compound may be a sigma receptor ligand that binds to, e.g., a σ1 receptor and/or a σ2 receptor with relatively high affinity and/or selectivity. For example, the benzofuran compound may be 5,6-dimethoxy-3-methyl-N-phenyl-N-(3-(piperidin-1-yl)propyl)benzofuran-2-carboxamide, 3-methyl-N-phenyl-N-(3-(piperidin-1-yl)propyl)benzofuran-2-carboxamide, or 6-methoxy-3-methyl-N-phenyl-N-(3-(piperidin-1-yl)propyl)benzofuran-2-carboxamide. The composition may include the benzofuran compound and a pharmaceutically acceptable carrier.

17 Claims, 6 Drawing Sheets

(56) References Cited

OTHER PUBLICATIONS

Guo et al. "The sigma-1 receptor protects against cellular oxidative stress and activates antioxidant response elements", Eur. J. Pharm. (2012),doi:10.1016/j.ejphar.2012.01.030.
Nguyen et al.,"Role of sigma-1 receptors in neurodegenerative diseases", J. Pharmacol. Science, 127:17-29 (2015).
Ruscher et al."The involvement of the sigma-1 receptor in neurodegeneration and neurorestoration", J. Pharmacol. Science, 127:30-35 (2015).
Marriott et al.,"σ-1 Receptor at the Mitochondrial-Associated Endoplasmic Reticulum Membrane is Responsible for Mitochondrial Metabolic Regulation", JPET, 343:578-86 (2012).
Marriott et al.,"Synthesis of N-phenyl-N-(3-(piperidin-1-yl)propyl)benzofuran-2-carboxamides as new selective ligands for sigma receptors", Bioorg. Med. Ch., 20:6856-61 (2012).
Hayashi et al.,"Cholesterol at the Endoplasmic Reticulum: Roles of the Sigma-1 Receptor Chaperone and Implications thereof in Human Diseases", Subcell Bioch., 51:381-98 (2010).
Bose et al.,"The pathophysiology and genetics of congenital lipoid adrenal hyperplasia", N. Engl. J. Med., 335:1870-78 (1996).
Miller et al.,"Early steps in steroidogenesis: intracellular cholesterol trafficking", J. Lipid Res., 52:2111-35 (2011).
Bose et al.,"Steroidogenic activity of StAR requires contact with mitochondrial VDAC1 and phosphate carrier protein", J. Biol. Ch., 283:8837-45 (2008).
Maurice et al.,"The Pharmacology of Sigma-1 Receptors", Pharmacol. Ther., 124:195-206 (2009).
Hayashi et al.,"Targeting ligand-operated chaperone sigma-1 receptors in the treatment of neuropsychiatric disorders", Expert Opin. Ther. Targets, 15:557-77 (2011).
Niso,"Sigma-2 Receptor: Biomarker for Solid Tumor Diagnosis and Target for Tumor Treatment", J. Cancer Biol. Res., 1:1007 (2013).
Marriott, K-S. C.,"Synthesis of Novel Agents for use in Addictive Treatment", NIH Grant No. DA027086 (Award Notice Date, Mar. 24, 2010).

* cited by examiner

BENZOFURAN COMPOUNDS, COMPOSITIONS, KITS AND/OR METHODS THEREOF

CROSS-REFERENCE TO RELATED APPLICATIONS

The present application claims the benefit of U.S. Provisional Patent Application No. 61/860,492, filed on Jul. 31, 2013, the contents of which is hereby incorporated by reference in its entirety.

STATEMENT REGARDING FEDERALLY SPONSORED RESEARCH OR DEVELOPMENT

This invention was made with government support under R03DA027086, 5P20MD003941, and/or RHD057876 awarded by the National Institutes of Health. The government has certain rights in the invention.

BACKGROUND

The sigma receptor includes at least two subtypes, σ1 and σ2. (Marriott et al., *JPET,* 343:578-586 (2012); Marriott et al., *Bioorg. Med. Chem.,* 20:6856-6861 (2012)). The sigma receptor is an intracellular receptor that is present throughout the human body, including the central nervous system and peripheral organs. (Marriott et al., *JPET,* supra.). For example, the mitochondria-associated endoplasmic reticulum (ER) membrane (MAM), which is known to physically associate with the outer mitochondria membrane (OMM), consists of ER subdomains enriched with σ1 receptors. (Hayashi and Su, *Subcell Biochem.,* 51:381-398 (2010).

The MAM may play an important role in supplying calcium to mitochondria as well as in lipid synthesis (e.g., phospholipids, cholesterol). (Hayashi and Su, *Subcell Biochem.,* 51:381-398 (2010). In addition, cholesterol transported from the OMM to the inner mitochondrial membrane (IMM) is the primary step (the rate-limiting step) in steroidogenesis. (Bose et al., *N. Engl. J. Med.,* 335:1870-1878 (1996); Marriott et al., *JPET,* supra.). Cholesterol is transported from the OMM to the IMM where it is catalyzed to form pregnenolone, which is subsequently transported back to the ER for the synthesis of several other steroids. (Miller and Bose, *J. Lipid Res.,* 52:2111-2135 (2011)). Transport of cholesterol to the site of steroidogenesis may be facilitated by steroidogenic acute regulatory protein (StAR), which interacts with voltage-dependent anion channel (e.g., VDAC1) at the OMM. (Bose et al., *J. Biol. Chem.,* 283: 8837-8845) (2008)). The sigma receptor may also play a role, as transfection of dominant-negative σ-1 receptors has been shown to disrupt the compartmentalization of cholesterol at the MAM. (Hayashi and Su, supra.).

The sigma receptor has also been investigated as a target for therapeutics in a variety of diseases. For example, the σ1 receptor has been investigated as a target for therapeutics in addiction, amnesia, pain, depression, Alzheimer's disease, schizophrenia, stroke, retinal neural degeneration, HIV infection, and cancer. (Maurice et al., *Pharmacol. Ther.,* 124:195-206 (2009); Hayashi et al., *Expert Opin. Ther. Targets,* 15:557-577 (2011)). In one example, the σ1 receptor ligand dimemorfan (with an affinity of 151 nM) has been shown to block the amnesic effects induced by $\beta_{25-35}$-amyloid peptide treatment in mice. (Maurice et al., supra.). In another example, the σ1 receptor ligand donepezil (with an affinity of 14.6 nM) has been used to treat Alzheimer's Disease. (Maurice et al., supra.). In a further example, σ2 ligands have been shown to induce cancer cell death, and combining σ2 receptor selective ligands with gemcitabine chemotherapy in vivo or with doxorubicin in several in vitro cancer cell lines demonstrated an additive effect in the blocking of tumor growth. (Niso, *J. Cancer Biol. Res.,* 1:1007 (2013).

BRIEF DESCRIPTION OF THE DRAWINGS

The various advantages of the embodiments of the present invention will become apparent to one skilled in the art by reading the following specification and appended claims, and by referencing the following drawings, in which:

DETAILED DESCRIPTION

Figure 1A:
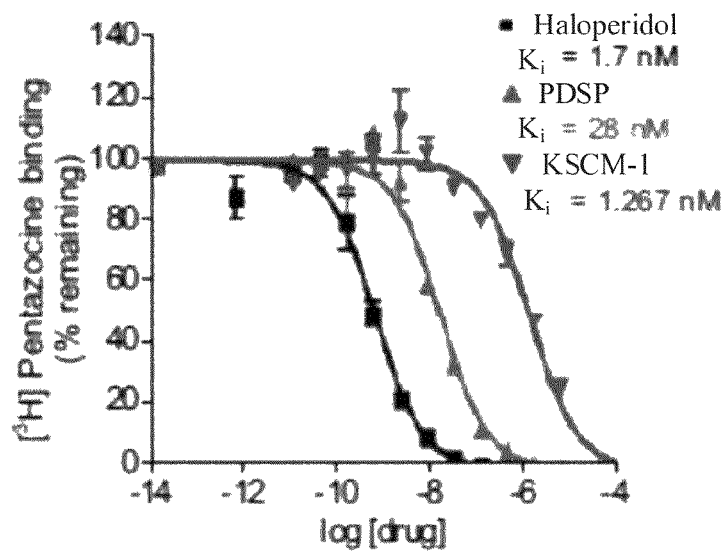
FIG. 1A to FIG. 1F are graphs of example secondary binding curves for $K_i$ determinations for 5,6-dimethoxy-3-methyl-N-phenyl-N-(3-(piperidin-1-yl)propyl)benzofuran-2-carboxamide (KSCM-1) (FIG. 1A, FIG. 1D), 3-methyl-N-phenyl-N-(3-(piperidin-1-yl)propyl)benzofuran-2-carboxamide (KSCM-5) (FIG. 1B, FIG. 1E), and 6-methoxy-3-methyl-N-phenyl-N-(3-(piperidin-1-yl) propyl)benzofuran-2-carboxamide (KSCM-11) (FIG. 1C, FIG. 1F) at σ1 and σ2 receptors, respectively, according to an embodiment.

Embodiments generally relate to benzofuran compounds, compositions thereof, kits thereof, and/or methods thereof. More particularly, embodiments may relate to a benzofuran-2-carboxamide moiety that is N-arylated and/or N-alkylated, a composition thereof, a kit thereof, and/or a method thereof. In one aspect of embodiments, a benzofuran compound may be a sigma receptor ligand that binds to, e.g., a σ1 receptor and/or a σ2 receptor. For example, the benzofuran compound may bind to the σ1 receptor and/or the σ2 receptor with relatively high affinity and/or selectivity.

In another aspect of embodiments, the benzofuran compound may be delivered to relatively increase lipid metabolism, relatively increase the expression of the σ1 receptor, relatively increase steroid hormone synthesis, relatively increase cholesterol metabolism and/or conversion, relatively increase the expression of StAR (and/or stabilize its expression), relatively increase an association between the σ1 receptor and VDAC2, relatively decrease the number of cells overexpressing the σ2 receptor, and so on. In a further aspect of embodiments, a benzofuran compound may be delivered to alleviate one or more symptoms of, and/or to reduce the relative severity (and/or likelihood) of, e.g., an endocrine disease, a neurological disease, cancer, and so on.

Embodiments may involve a compound of Formula I:

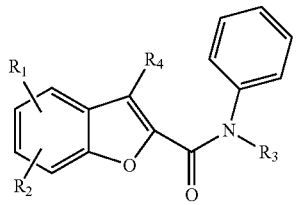

An alkyl of the compound of Formula I may refer to an aliphatic hydrocarbon group having one of its hydrogen atoms replaced with a bond. An alkyl of the compound of Formula I may be linear (straight) or branched. An alkyl of the compound of Formula I may be unsubstituted or substituted by one or more substituents that may be the same or different. For example, one or more hydrogen atoms on a designated atom of an alkyl may be replaced provided that the designated atom's valency is maintained. Non-limiting examples of substituents that may be independently selected for an alkyl include halo, aryl, cycloalkyl, hydroxy, —O-alkyl, —O-aryl, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH, and —C(O)O-alkyl. A halo substituent may be a halogen such as, for example, —F, —Cl, —Br, and —I. An aryl substituent may be an aromatic monocyclic or multicyclic ring system comprising from about 6 carbon atoms to about 14 carbon atoms, which may include one or more ring substituents that are the same or different. For example, the aryl group may be phenyl. A cycloalkyl substituent may be a non-aromatic mono- or multicyclic ring system comprising from about 3 carbon atoms to about 10 carbon ring carbon atoms, which may include one or more ring substituents that are the same or different.

An alkyl of the compound of Formula I may refer to an alkyl containing carbon atoms in a range of about 1 carbon atom to about 20 carbon atoms ($C_{1-20}$-alkyl). Non-limiting examples of a $C_{1-20}$-alkyl include methyl, ethyl, n-propyl, isopropyl, n-butyl, sec-butyl, isobutyl, tert-butyl, n-pentyl, neopentyl, isopentyl, n-hexyl, isohexyl, neohexyl, and so on. For example, $R_1$, $R_2$, and/or $R_4$ of the compound of Formula I may be methyl, ethyl, and so on. An alkoxy group (O-alkyl) of the compound of Formula I may refer to an alkyl group singular bonded to oxygen. For example, $R_1$ and/or $R_2$ of the compound of Formula I may be methoxy ($C_1$-alkoxy, O—$C_1$-alkyl), ethoxy ($C_2$-alkoxy, O—$C_2$-alkyl), and so on. An N-alkyl group of the compound of Formula I may refer to an alkyl group singular bonded to nitrogen. For example, $R_3$ of the compound of Formula I may be (piperidin-1yl)methyl, 3-(piperidin-1yl)propyl, and so on. A functional group of the compound of Formula I may be a formyl group (COH), a carboxyl group (COOH), and so on. For example, $R_4$ of the compound of Formula I may be a carboxyl group. Thus, the term alkyl as used herein may refer to an alkyl group as well as an alkyl portion such as, for example, an alkyl portion of a haloalkyl, of an alkoxy, and so on.

In one example, $R_1$ and $R_2$ may be independently selected from $C_{1-2}$-alkyl, $C_{1-2}$-alkoxy, and hydrogen, $R_3$ may be independently selected from (piperidin-1yl)$C_{1-5}$-alkyl, and $R_4$ may be independently selected from $C_{1-2}$-alkyl, a formyl group, a carboxyl group, and hydrogen. Thus, the compound of Formula I may be 5,6-dimethoxy-3-methyl-N-phenyl-N-(3-(piperidin-1-yl)propyl)benzofuran-2-carboxamide (KSCM-1), 3-methyl-N-phenyl-N-(3-(piperidin-1-yl)propyl)benzofuran-2-carboxamide (KSCM-5), 6-methoxy-3-methyl-N-phenyl-N-(3-(piperidin-1-yl) propyl)benzofuran-2-carboxamide (KSCM-11), and so on.

A salt of the compound of Formula I may refer to an acidic salt (e.g., formed with inorganic acid, organic acid), a basic salt (e.g., formed with inorganic base, organic base), a covalent-bonded salt, an ionic salt, a zwitterionic salt, a pharmaceutically acceptable salt (e.g., non-toxic salt, physiologically acceptable salt), and so on. A salt may be formed by, for example, reacting a benzofuran compound with an amount of acid or base (e.g., an equivalent amount) in a medium such as one in which the salt precipitates, in an aqueous medium followed by lipoophilization, and so on. Thus, for example, one aspect of embodiments may include a salt of KSCM-1, of KSCM-5, of KSCM-11, of prodrugs thereof, or isomers thereof, and so on. In one example, the salt may include a hydrochloride or sulfate of KSCM-1, of KSCM-5, of KSCM-11, of prodrugs thereof, of isomers thereof, and so on.

A prodrug (e.g., a drug precursor) of the compound of Formula I may refer to a compound that is transformed (e.g., in vivo) to provide the compound of Formula I, for an intended pharmacological effect, by various intracellular and extracellular mechanisms (e.g., metabolic process, chemical process) such as, for example, through hydrolysis in body fluid (e.g., blood, cytoplasm). Accordingly, for example, a prodrug may be administered in an inactive or less than fully active form of the compound of Formula I and be converted to the active form represented by the compound of Formula I. In one example, a protective group (e.g., non-toxic protective group) may be utilized in a transient manner, which may be directly linked or indirectly linked (e.g., via a succinic spacer, an amino acid spacer) to the compound of Formula I (e.g., via a functional group) and removed by various intracellular or extracellular mechanisms. In another example, a composition including the compound of Formula I and a pharmaceutically acceptable carrier that operates as a protective group may be utilized to provide a prodrug, discussed below. Thus, one aspect of embodiments may include a prodrug of KSCM-1, of KSCM-5, of KSCM-11, of salts thereof, of isomers thereof, and so on. In one example, a prodrug strategy may include N-acylation of, e.g., the compound of Formula I (e.g., KSCM-1, KSCM-5, KSCM-11) using for example an acetyl functional group to assist in lipophilicity and/or penetration of the blood brain barrier (BBB).

An isomer of the compound of Formula I may refer to a constitutional isomer (e.g., same chemical formula with different connectivity) or a stereoisomer (e.g., same chemical formula with same connectivity). The stereoisomer may include a conformational isomer (e.g., interconvertable by rotation about single bonds) or a configurational isomer (e.g., not interconvertable by rotation about single bonds). The configurational isomer may include a geometric isomer (e.g., isomerism at double bonds) or an optical isomer (e.g., no isomerism at double bonds). The optical isomer may include a diastereomer (e.g., not non-superimposable mirror images) or an enantiomer (e.g., non-superimposable mirror images). Thus, for example, cis- and trans-forms (and mixtures) are contemplated, such as when the compound of Formula I includes a double bond or a fused ring.

In one example where $R_1$ and $R_2$ of the compound of Formula I are not hydrogen, $R_1$ and $R_2$ may be in ortho substitution to occupy positions next to each other on the benzene ring (e.g., positions 5,6). In another example, $R_1$ and $R_2$ of the compound of Formula I may be in meta substitution to occupy positions spaced apart from each other on the benzene ring (e.g, positions 5,7). In a further example, $R_1$ and $R_2$ of the compound of Formula I may be in para substitution to occupy positions opposite each other on the benzene ring (e.g., positions 4,7). Thus, one aspect of embodiments may include an isomer of KSCM-1, of KSCM-5, of KSCM-11, of salts thereof, of prodrugs thereof, and so on. In addition, isomers generally may be substantially free of other isomers, or may be admixed, for example, as racemates or with all other, or other selected, isomers. Also, for example when only one of $R_1$ and $R_2$ of the compound of Formula I is not hydrogen, the non-hydrogen $R_1$ or $R_2$ may occupy any position on the benzene ring (e.g., positions 4-7).

Embodiments may involve a composition including the compound of Formula I and a pharmaceutically acceptable carrier such as, for example, a non-toxic carrier, a physiologically acceptable carrier, and so on. Notably, while compositions below feature the compound of Formula I, compositions contemplated are not limited thereto and may additionally or alternatively involve salts thereof, prodrugs thereof, isomers thereof, or combinations thereof.

The pharmaceutically acceptable carrier may include an organic and/or inorganic material. In one example, the pharmaceutically acceptable carrier may include an emulsion, a paste, a cream, a lotion, a gel, jelly, ointment, oil, aerosol, powder, solvent, and so on. In another example, the pharmaceutically acceptable carrier may include a liposome, a micelle, a peptide (e.g., albumin), a synthetic polymer (e.g., polyethylene glycol), a natural polymer (e.g., hyaluronic acid, dextran, chitosan), and so on. In a further example, the pharmaceutically acceptable carrier may include an n-dimensional material (where n=0, 1, 2, 3) such as, for example, a 0-dimensional nanomaterial (e.g., quantum dot, nanoparticle), a 1-dimensional nanomaterial (e.g., a nanotube, a nanorod), a 2-dimensional nanomaterial (e.g., a quantum well, a film), a 3-dimensional material, such as a matrix (e.g., polymeric matrix such as polyethylene glycol (PEG)), and so on.

The pharmaceutically acceptable carrier may be linked with (e.g., covalently linked, electrostatically linked) and/or may physically sequester (e.g., physically trap in a core, in physical crosslinks) the compound of Formula I. Accordingly, for example, the compound of Formula I may be linked or otherwise associated with the pharmaceutically acceptable carrier until one or more bonds and/or links disassociate (e.g., break, swell). In this regard, the pharmaceutically acceptable carrier may operate as a protective group that is linked or otherwise associated with the compound of Formula I to form a prodrug thereof, wherein bonds and/or links disassociate over time to form and/or release the compound of Formula I for a therapeutic effect. Thus, for example, the pharmaceutically acceptable carrier may form an implantable composition, ingestible composition, topical composition, etc., to provide, e.g., immediate release, timed release, and so on.

The pharmaceutically acceptable carrier may operate to modulate the pharmacokinetic properties (e.g., absorption, distribution, metabolism, excretion) and/or the pharmacodynamic properties (e.g., concentration at the site of action, resulting effect) of the compound of Formula I. For example, the pharmaceutically acceptable carrier may facilitate transport across the BBB when the desired target cell includes a neuron, a glial cell, and so on. Alternatively, properties (e.g., moieties, substituents, dimensions) of the pharmaceutically acceptable carrier may be tailored to substantially prevent transport across the BBB. The compound of Formula I and/or the pharmaceutically acceptable carrier may also be functionalized with a ligand specific for a particular tissue type (e.g., an antibody for a particular cell type to facilitate target specificity), with a ligand involved in receptor mediated endocytosis, with a substituent to facilitate lipid membrane solubility, and so on. In addition, the pharmaceutically acceptable carrier may modulate bioavailability by, for example, providing immediate and/or timed release (e.g., a tablet), providing extracellular enzymatic protection (e.g., a depot, a liposome), providing intracellular activation (e.g., a releasable protective group linked via a functional group), and so on. Thus, the pharmaceutically acceptable carrier may facilitate target specificity, modulate concentration at a target site, modulate activity, modulate efficacy, and so on.

Embodiments may involve a composition including the compound of Formula I and one or more other therapeutic compounds. For example, a composition may include the compound of Formula I, a pharmaceutically carrier, and/or one or more of a neuroprotective drug and an anticancer drug. In one example, a composition may include the compound of Formula I and one or more of an Alzheimer's Disease drug, a Parkinson's Disease drug, a depression drug, and an antipsychotic drug. For example, the composition may include one or more of donepezil hydrochloride, galantamine, memantine, latrepirdine, bapineuzumab, semagacestat, solanezumab, gammaglobulin IV, CERE-110, ACC-001, PF-4360365, NIC5-15, R3487, rivastigmine, tacrine, levodopa, citalopram, escitalopram, paroxetine, fluoxetine, vortioxetine, sertraline, venlafaxine, amitriptyline, phenelzine, and clozapine. Thus, for example, donepezil hydrochloride may be provided to prevent the breakdown of acetylcholine, which is important in for the process of memory, thinking, reasoning, and which is used to treat mild to moderate dementia caused by Alzheimer's Disease. In addition, memantine may be provided as an NMDA receptor blocker, PF-4360365 may be provided as anti-beta amyloid, and so on.

In another example, a composition may include the compound of Formula I and one or more of a lung cancer drug, a liver cancer drug, an adrenal cancer drug, a pancreatic cancer, a spleen cancer drug, a bladder cancer drug, a breast cancer drug, and a bone cancer drug. For example, the composition may include one or more of gemcitabine, doxorubicin, cyclophosphamide, gemcitabine, carboplatin, and imatinib. Thus, for example, gemcitabine may be provided to arrest tumor growth and cause apoptosis in a variety of cancer types (e.g., lung cancer). In addition, carboplatin may be provided to interact with deoxyribonucleic acid (DNA) and DNA repair in a variety of cancer types (e.g., ovarian carcinoma, lung, head and neck cancers, endometrial, esophageal, bladder, breast and cervical cancers, central nervous system cancers, germ cell tumors, and osteogenic sarcoma). Accordingly, any other therapeutic compound may be included to provide additive and/or supplemental therapeutic effects when the compound of Formula I is delivered.

The compound of Formula I may also be delivered to a cell to drive lipid metabolism (e.g., cholesterol conversion, steriodogenesis) via native metabolic processes (e.g., regulation of cytochrome P450 enzyme, 3-beta-hydroxysteroid dehydrogenase, 21-hydroxylase, 11-beta-hydroxylase, aromatase, and 5-alpha-reductase). Thus, for example, a composition may include the compound of Formula I and one or more therapeutic compounds that modulate native metabolic processes. In one example, the composition may include the compound of Formula I and trilostane, a known inhibitor of 3-beta-hydroxysteroid dehydrogenase, to drive the native metabolic processes towards androgen production. In another example, the composition may include the compound of Formula I and adrenocorticotropic hormone (ACTH), a known compound to increase the expression of 11-beta-hydroxylase, to drive the native metabolic processes towards corticosterone production. It should be understood that a first composition including the compound of Formula I and a pharmaceutically acceptable carrier may also be provided together with a second composition including one or more other therapeutic compounds and a pharmaceutically acceptable carrier, which may be the same or different than that used in the first composition.

Particular dosages (e.g., effective amounts), number, and frequency of administration can be determined routinely. For example, the quantities of the compound of Formula I may be adjusted and determined routinely, e.g., to eliminate or reduce adverse reactions, depending on the health of the patient receiving treatment, depending on affinity of other therapeutic sigma receptor ligands and/or use for a particular disease, etc. Thus, effective amounts may, for example, be the same or different than amounts used for other sigma receptor ligands having the same and/or similar affinity for the same and/or similar purpose. In one example, donepezil has been shown to be effective in controlled clinical trials at doses of about 5 mg to about 23 mg administered orally once daily; namely, 5 mg to treat mild to moderate Alzheimer's Disease, 10 mg and 23 mg to treat moderate to severe Alzheimer's Disease. Since the σ1 receptor ligand donepezil has an affinity of 14.6 nM for the σ1 receptor, the quantity of a particular compound of Formula I that is utilized for Alzheimer's Disease may be adjusted and determined routinely using e.g., 5 mg to about 23 mg administered orally once daily. For example, 10 mg of KSCM-1 (with an affinity of 27 nM) for the σ1 receptor, administered orally once daily, may initially be used for mild to moderate Alzheimer's Disease (e.g., double dosage based on half affinity).

However, initial formulations (e.g., carriers) and/or concentrations may be routinely adjusted (e.g., concentration adjusted up or down) based on efficacy, toxicity, etc., which are routinely determinable. For example, slow release formulations for a 10 mg dose of KSCM-1 may provide approximately 1 nM or less at a target site to provide desired e.g., cell viability, may provide approximately 10 nM at a target site to provide desired e.g., cholesterol conversion, and so on. In another example, formulations may be generated to provide between about 1 nM and 100 nM (or less or more) of KSCM-5 at a particular target for to provide, e.g., cell death for cancer cells overexpressing the σ2 receptor.

Embodiments may involve an apparatus including the compound of Formula I, the pharmaceutically acceptable carrier, a composition including the compound of Formula I and the pharmaceutically acceptable carrier, and so on. For example, an implantable apparatus may include a processor (e.g., microcontroller, logic, integrated circuit), a network interface (e.g., an antenna), and/or a chamber to maintain the compound of Formula I, a composition including the compound of Formula I and the pharmaceutically acceptable carrier, and so on. In this regard, a control signal may cause the implantable apparatus to release its payload, wherein the control signal may be dynamically generated (e.g., in response to an environmental condition) and/or periodically generated (e.g., based on need, based on a predetermined schedule). The pharmaceutically acceptable carrier may also operate as a membrane to seal the chamber and degrade (e.g., in response to a control signal, in response to an environmental condition) for facilitating the release of, e.g., the compound of Formula I from the chamber of the apparatus.

Embodiments may involve a method of making the compound of Formula I. In one example, commercially available coumarins (e.g., 6,7-hydroxy-coumarin) may be modified (e.g., $C_{1-20}$-alkylated, $C_{1-20}$-alkoxylated) and subsequently halogenated (e.g., brominated at position 3). For example, a solution of iodomethane, potassium carbonate and acetone, followed by a solution of bromine and dichloromethane, may be used produce, e.g., 6,7-di-methoxy-4-methyl-3-bromocoumarin from 6,7-hydroxy-coumarin. Notably, 3-bromocoumarins may undergo base-catalyzed Perkin rearrangement, which may require approximately 3 hours reflux quantitatively to yield benzofuran-2-carboxylic acids. Such reactions may involve utilizing sodium hydroxide and ethanol to form e.g., 5,6-di-methoxy-3-methyl-benzofuran-2-carboxylic acid from 6,7-di-methoxy-4-methyl-3-bromo-coumarin. It should be understood that, e.g., hydrogen may ultimately occupy positions 3, 4, 5, 6, and/or 7 in a benzofuran-2-carboxylic acid as desired, such as where reaction conditions are readily modified by providing, e.g., 6,7-di-methoxy-3-bromocoumarin for 5,6-di-methoxy-benzofuran-2-carboxylic acid, 3-bromocoumarin for benzofuran-2-carboxylic acid, and so on.

In another example, a microwave-assisted expedited synthetic pathway may be utilized to yield one or more benzofuran-2-carboxylic acids in quantitative yields from 3-bromocoumarins. For example, a Perkin rearrangement reaction of mono- and di-alkoxy-4-alkyl-3-bromocoumarins such as mono- and di-$C_{1-20}$-alkoxy-4-$C_{1-20}$-alkyl-3-bromocoumarins may provide quantitative yields of mono- and di-$C_{1-20}$-alkoxy-3-$C_{1-20}$-alky-benzofuran-2-carboxylic acids. In one example, mono- and di-hydroxy-coumarins (e.g., 6,7-hydroxy-coumarin) may be alkylated (e.g., methylated at positions 7, 6, and 4), discussed above, and then subsequently halogenated (e.g., brominated at position 3) via a microwave-assisted regioselective bromination with N-bromosuccinimide (NBS) to yield, e.g., 6,7-$C_{1-20}$-alkoxy-4-$C_{1-20}$-alkyl-3-bromocoumarns (e.g., 6,7-methoxy-4-methyl-3-bromocoumarin) in relatively high yields (e.g., approximately 85-89% yields) under microwave reaction conditions of NBS as brominating agent and acetonitrile as solvent at 250 W for a period of approximately 5 min. Thereafter, benzofuran-2-carboxylic acids may be generated under microwave reaction conditions utilizing sodium hydroxide and ethanol at 300 W for a period of approximately 5 minutes. Thus, for example, 6,7-methoxy-4-methyl-3-bromocoumarin may provide 5,6-methoxy-3-methyl-2-carboxylic acid under such microwave reaction conditions.

In addition, benzofuran-2-carboxylic acids may be N-arylated. For example, 3-$C_{1-20}$-alkyl-N-phenylbenzofuran-2-carboxamides may be produced by reacting aniline with 3-$C_{1-20}$-alkyl-benzofuran-2-carboxylic acids (e.g., 3-methyl-benzofuran-2-carboxylic acid). In one example, aniline may be reacted with mono- and di-$C_{1-20}$-alkoxy-3-$C_{1-20}$-alkyl-benzofuran-2-carboxylic acids (e.g., for mono- and di-methoxy-3-methyl-N-phenylbenzofuran-2-carboxamides) in the presence of e.g., dicyclohexylcarbodiimide (DCC), dimethylaminopryidine (DMAP), and dichloromethane at room temperature. Similarly, for example, 3-$C_{1-20}$-alkyl-N-phenylbenzofuran-2-carboxamides (e.g., 3-methyl-N-phenylbenzofuran-2-carboxamide) may be generated by condensing commercially available 3-$C_{1-20}$-alkyl-benzofuran-2-carboxylic acids (e.g., 3-methyl-benzofuran-2-carboxylic acid) with aniline.

In addition, benzofuran-2-carboxylic acids may be N-alkylated. In one example, a desired group may be introduced at a nitrogen of a carboxamide via a nucleophillic substitution when treated with sodium hydride (NaH) and an appropriate halogenated amine (e.g., chloro-propylpiperdine) to yield a benzofuran-2-carboxylic acid that is N-alkylated. In another example, synthesis of, e.g., mono- and di-$C_{1-20}$-alkyoxy-3-$C_{1-20}$-alkyl-N-phenyl-N-(3-(piperidin-1-yl)$C_{1-20}$-alkyl)benzofuran-2-carboxamides (e.g., KSCM-11, KSCM-1) may be achieved by treating carboxamides (e.g., 3-$C_{1-20}$-alkyl-N-phenylbenzofuran-2-carboxamides such as 5-methoxy-3-methyl-N-phenylbenzofuran-2-carboxamide) with a NaH, followed by N-alkylation with, e.g., 1-(3-iodo-$C_{1-20}$-alkyl)piperidine. For example, a modified halogen exchange Finkelstein reaction may be employed to convert commercially available 1-(3-chloropropyl)piperidine hydrogen chloride salt in the presence of potassium iodide (KI), tetrabutylammonium bromide (TBAB), and potassium carbonate ($K_2CO_3$) into the relatively more reactive iodopropylpiperidine in situ, which may then react with anions obtained from treating carboxamides with NaH to produce, e.g., KSCM-11 and KSCM-1. Similarly, for example, KSCM-5 may be synthesized by N-alkylation of a carboxamide (e.g., 3-methyl-N-phenylbenzofuran-2-carboxamide) with, e.g., 1-(3-iodopropyl)piperidine.

In addition, benzofuran-2-carboxylic acids that have been N-arylated and/or N-alkylated may be functionalized. For example, benzofuran-2-carboxylic acids such as KSCM-1, KSCM-5, and/or KSCM-5 may undergo photo-initiated free radical allylic halogenation (e.g., bromination) to yield an allyl halide (e.g., allyl bromide) such as, e.g., mono- and di-$C_{1-20}$-alkoxy-3-$C_{1-20}$-haloalkyl-N-phenyl-N-(3-(piperidin-1-yl)$C_{1-20}$-alkyl)benzofuran-2-carboxamides. In one example, an allylic bromide may be generated using NBS, carbon tetrachloride, and light, wherein subsequent oxidation affords functionalization. In particular, subsequent oxidation of an allylic bromide using trimethylamine N-oxide and dimethyl sulfoxide in ambient temperature followed by N-bromosuccinimide, carbon tetrachloride, light, and water affords carboxylic acid functionalization, e.g., at position 3. The functional group (e.g., carboxyl group) may be free and/or may be utilized for a variety of purposes, such as to provide a salt, to provide isomerism, to be linked with a protective group to generate a prodrug, to be linked with a pharmaceutically acceptable carrier, to be linked with a ligand providing target specificity, to be linked with a spacer, etc., using, e.g., well known processes, groups, and/or carriers for functional group (e.g., carboxylic acid) chemistry.

Embodiments may involve a kit including the compound of Formula I. Notably, while kits below feature the compound of Formula I, kits contemplated are not limited thereto and may additionally or alternatively involve salts thereof, prodrugs thereof, isomers thereof, compositions thereof, or combinations thereof.

A kit may include a container to hold the compound of Formula I. The container may be formed of any suitable material. For example, the container may be formed of a metal material, a polymeric material (e.g., plastic), and so on. The container may include a dispenser portion, such as an opening that is accessed via a removable cap (e.g., a threaded cap), a nozzle (e.g., an inhaler nozzle), a removable film (e.g., a patch film), a perforated surface (e.g., a tablet package perforated surface), an injection surface (e.g., a fluid drawing surface of a vial), and so on. Thus, the container may include a chamber to maintain the compound of Formula I, which may be accessed via the dispenser portion of the container for repeated use or for single use.

The container may be associated with an instruction regarding the compound of Formula I, such as a storage instruction (e.g., a storage condition), a use instruction (e.g., administration regimen, implant process), a disposal instruction, a warning, and so on, or combinations thereof. The container may also be associated with information regarding the compound of Formula I, such as a chemical formula, a structural formula, a property (e.g., molecular weight, melting point, concentration, etc.), an expiration date, and so on. The container may include a label to provide the instruction and/or the information regarding the compound of Formula I. The instruction and/or the information may also be accessible from data storage, such as a computer server, computer readable medium, a database structure, and so on. For example, the instruction and/or the information may be in any data format, such as a text editor format (RTF), an image format (JPEG), a portable document format (PDF), a markup language format (HTTP, XML), a spreadsheet format, and so on.

Accordingly, the container may be a pill bottle, an inhaler, a transdermal patch, an eye drop bottle, a vial and/or a syringe in a box, and so on. In this regard, a label may be physically attached or otherwise associated with the container to provide instructions related to, e.g., an administration regimen. In another example, the container may be a laboratory storage container, a transport container, and so on. In this regard, a label may be physically attached or otherwise associated with the container to provide instructions related to, e.g., suitable storage conditions (e.g., pressure, temperature), hazard warnings, and so on, or combinations thereof. Thus, it should be understood that a first composition including the compound of Formula I and a pharmaceutically acceptable carrier may be provided together with a second composition including one or more other therapeutic compounds and a pharmaceutically acceptable carrier, which may be the same or different than that used in the first composition, in the same or different kit, container, and so on, which may include respective instructions and/or information via the same or different label, data storage device (e.g., memory), and so on.

Embodiments may involve a method including administering the compound of Formula I to a subject. Notably, while methods below feature the compound of Formula I, methods contemplated are not limited thereto and may additionally or alternatively involve salts thereof, prodrugs thereof, isomers thereof, compositions thereof, or combinations thereof.

The subject may include, for example, a cell, a mammal, a human, and so on. For example, the cell may be in vitro and/or in vivo. In one example, the method may include administering the compound of Formula I to a cultured cell in vitro in a dish, a flask, a plate, a well, and so on. In this regard, the compound of Formula I may be administered via, for example, a pipette. In another example, the method may also include administering the compound of Formula I to a cell in vivo. In this regard, any suitable route of administration may be implemented. For example, administration to a mammal, a human, etc., may include utilizing a lotion for a topical route of administration, a solvent for an injection route of administration, an aerosol for an inhalation route of administration, and so on. Thus, the compound of Formula I may be administered to a cell in vivo using, for example, a capsule, a tablet, a syringe, an inhaler, a patch, a dropper (e.g., eye dropper), and so on.

A method may include administering the compound of Formula I in an effective amount to elicit a biological or medicinal response in a tissue, system, animal, human, and so on. In one example, an effective amount may include a therapeutically effective amount for the alleviation of one or more symptoms of a disease, a condition treated, and so on. In another example, an effective amount may include a prophylactically effective amount for a reduction of a severity and/or likelihood of one or more symptoms of a disease or condition. For example, the compound of Formula I may be administered in an effective amount to modulate lipid metabolism, relatively increase the expression of a $\sigma 1$ receptor, relatively increase steroid hormone synthesis, relatively increase cholesterol conversion, relatively increase the expression of StAR (and/or stabilize its expression), relatively increase an association between a $\sigma 1$ receptor and VDAC2, relatively decrease the number of cells overexpression the $\sigma 2$ receptor, and so on. The compound of Formula I may also be administered in an effective amount to alleviate of one or more symptoms of, or to reduce the relative severity and/or likelihood of, e.g., an endocrine disease, a neurological disease, cancer, and so on.

A method may include administering the compound of Formula I to a subject to increase the expression of $\sigma 1$ receptor. Thus, for example, a composition including the compound of Formula I and a pharmaceutically acceptable carrier may be administered to a subject. A method may include administering the compound of Formula I to the subject to increase steroid hormone synthesis. In one example, a composition including the compound of Formula I and the pharmaceutically acceptable carrier may be administered. The method may include, for example, increasing the synthesis of progesterone. A method may include administering the compound of Formula I to the subject to increase cholesterol metabolism. In one example, a composition including the compound of Formula I and a pharmaceutically acceptable carrier may be administered. The method may include, for example, increasing the conversion of cholesterol to pregnenolone.

Accordingly, a method including administering the compound of Formula I to a subject may involve a combination of benefits. For example, administration of KSCM-1 may enhance cholesterol transport into the mitochondria. Cholesterol transport into the mitochondria may be needed for synthesis of a steroid hormone. In addition, cholesterol may be an important compound for the survival of substantially all species, and/or may be implicated in the onset and/or progression of neurological disorders, developmental disorders, and so on. Thus, for example, at least KSCM-1 may be used as a drug at least to enhance cholesterol trafficking for a variety of purposes and/or benefits.

A method may include identifying a subject in need of increased expression of the $\sigma 1$ receptor, increased steroid hormone synthesis (and/or stabilization of its synthesis), increased cholesterol metabolism (and/or stabilization of its metabolism), and so on. The subject in need may include, for example, a cell, a mammal, a human, and so on. In one example, the subject in need may include a subject with a neurological disease such as Alzheimer's Disease. For example, Alzheimer's Disease may require that a precursor compound bind to available cholesterol, wherein increased cholesterol metabolism may operate to minimize Alzheimer's Disease onset, progression, and so on. The method may also include administering, in response to the identification of the subject in need, the compound of Formula I, a composition including the compound of Formula I and a pharmaceutically acceptable carrier, and so on.

A method may include identifying a susceptible subject to a disease involving the $\sigma 1$ receptor, steroid synthesis, cholesterol metabolism, and so on. The susceptible subject may include, for example, a cell, a mammal, a human, and so on, or combinations thereof. In one example, the susceptible subject may include a subject with a marker for a neurological disease such as Alzheimer's Disease. For example, the susceptible subject may have amyloid precursor protein (APP), beta-amyloid, and so on. The method may also include administering, in response to the identification of the susceptible subject, the compound of Formula I, a composition including the compound of Formula I and a pharmaceutically acceptable carrier, and so on.

A method may include administering, e.g., at least KSCM-1 to a subject to increase the expression of StAR (and/or stabilization of its expression). In one example, a composition including, e.g., at least KSCM-1 and a pharmaceutically acceptable carrier may be administered. The subject may include, for example, a cell, a mammal, a human, and so on, or combinations thereof. A method may include increasing an association between $\sigma 1$ receptor and VDAC2 to enhance cholesterol loading onto the OMM. For example, while there may be more than 73% amino acid identity between VDAC1 and VDAC2, and/or while they may be present at substantially the same position of the outer mitochondrial membrane, the $\sigma 1$ receptor may only specifically recognize VDAC2. Thus, increasing the expression of the $\sigma 1$ receptor and/or StAR may enhance cholesterol loading onto the OMM.

A method may include identifying a subject in need of increased expression of StAR (and/or stabilization of its expression), a susceptible subject to a disease involving StAR, and so on. The subject in need and/or the susceptible subject may include, for example, a cell, a mammal, a human, and so on. In one example, the subject in need and/or the susceptible subject may include an Alzheimer's Disease patient. The method may also include administering, in response to the identification, at least KSCM-1, a composition including KSCM-1 and a pharmaceutically acceptable carrier, and so on.

A method may include administering, e.g., at least KSCM-5 and/or KSCM-11 to a subject to minimize the number of cells overexpressing the σ2 receptor. In one example, a composition including at least two or more of KSCM-5, KSCM-11, and a pharmaceutically acceptable carrier may be administered. The subject may include, for example, a cell, a mammal, a human, and so on, or combinations thereof. In one example, toxicity for healthy cells with basal expression (e.g., normal, usual) of the σ1 receptor and/or the σ2 receptor may be minimized since a relatively low dosage may be administered as a result of a relatively high ligand affinity for the σ2 receptor, a greater probability of encountering the σ2 receptor due to the overexpression of the σ2 receptor in target cells (e.g., cancer cells), targeted delivery (e.g., via catheter, syringe), and so on.

A method may include identifying a subject in need of minimizing the number of cells overexpressing of the σ2 receptor, a susceptible subject to a disease involving cells overexpressing the σ2 receptor, and so on. The subject in need and/or the susceptible subject may include, for example, a cell, a mammal, a human, and so on, or combinations thereof. In one example, the subject in need and/or the susceptible subject may include a breast cancer patient, a pancreatic cancer patient, a renal carcinoma patient, a sarcoma patient, a lung cancer patient, and so on. The method may also include administering, in response to the identification, e.g., at least KSCM-5 and/or KSCM-11, a composition including at least two or more of KSCM-5, KSCM-11, and a pharmaceutically acceptable carrier.

Example Embodiment 1

Ligand Synthesis

A microwave-assisted synthetic pathway may be utilized as follows, wherein reagents for step (a include DCC, DMAP, aniline, and $CH_2Cl_2$, and wherein reagents for step (b include NaH, 1-(3-chloropropyl)piperdine HCl, $K_2CO_3$, KI, TBAB, and $CH_2Cl_{12}$:

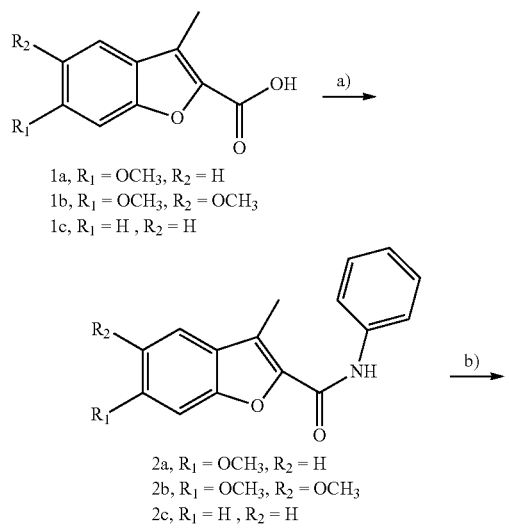

1a, $R_1$ = $OCH_3$, $R_2$ = H
1b, $R_1$ = $OCH_3$, $R_2$ = $OCH_3$
1c, $R_1$ = H, $R_2$ = H

2a, $R_1$ = $OCH_3$, $R_2$ = H
2b, $R_1$ = $OCH_3$, $R_2$ = $OCH_3$
2c, $R_1$ = H, $R_2$ = H

-continued

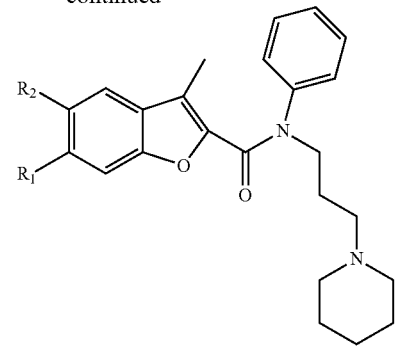

KSCM-11, $R_1$ = $OCH_3$, $R_2$ = H
KSCM-1, $R_1$ = $OCH_3$, $R_2$ = $OCH_3$
KSCM-5, $R_1$ = H, $R_2$ = H

The microwave-assisted expedited synthetic pathway may involve the preparation of 3-methylbenzofuran-2-carboxylic acids (1a and 1b) in quantitative yields via a Perkin rearrangement reaction of mono- and di-methoxy-3-bromocoumarins. Mono- and di-hydroxycoumarins were methylated and subsequently brominated at position-3 via a microwave-assisted regioselective bromination with N-bromosuccinimide (NBS) to yield mono- and di-methoxy-3-bromocoumarins in 85-89% yields.

3-Bromocoumarins traditionally undergo base-catalyzed Perkin rearrangement, which requires 3 hours reflux quantitatively yielding benzofuran-2-carboxylic acids. However under microwave reaction conditions these reactions were completed in 5 min. Mono- and di-methoxy-3-methyl-N-phenylbenzofuran-2-carboxamides (2a and 2b) were produced by reacting aniline with the corresponding 3-methylbenzofuran-2-carboxylic acids (1a and 1b) in the presence of DCC and DMAP at room temperature, discussed above. 3-Methyl-N-phenylbenzofuran-2-carboxamide (2c) was produced by condensing commercially available 3-methylbenzofuran-2-carboxylic acid (1c) with aniline.

Syntheses of mono- and di-methoxy-3-methyl-N-phenyl-N-(3-(piperidin-1-yl)propyl)benzofuran-2-carboxamides (KSCM-11 and KSCM-1) was achieved by treating carboxamides (2a and 2b) with NaH followed by N-alkylation with 1-(3-iodopropyl)piperidine. A modified halogen exchange Finkelstein reaction was employed to convert commercially available 1-(3-chloropropyl)piperidine hydrogen chloride salt in the presence of potassium iodide, tetrabutylammonium bromide (TBAB) and potassium carbonate into the more reactive iodopropylpiperidine in situ, which then reacted with anions obtained from treating carboxamides (2a and 2b) with sodium hydride producing KSCM-11 and KSCM-1. 3-methyl-N-phenyl-N-(3-(piperidin-1-yl)propyl)benzofuran-2-carboxamide (KSCM-5) was similarly synthesized by N-alkylation of carboxamide (2c) with 1-(3-iodopropyl)piperidine.

Accordingly, the synthesis of 3-methyl-N-phenyl-N-(3-(piperidin-1-yl)propyl)benzofuran-2-carboxamides (e.g., KSCM-1, KSCM-5, KSCM-11) may be achieved by treating carboxamides (2a, 2b, 2c) with NaH followed by N-alkylation with 1-(3-iodopropyl)piperidine via a new modified halogen exchange Finkelstein reaction which may convert commercially available 1-(3-chloropropyl)piperidine hydrogen chloride salt in the presence of KI, TBAB, and $K_2CO_3$ into the more reactive iodopropylpiperidine in situ, which may be reacted with anions obtained from treating carboxamides (2a, 2b, 2c) with NaH to produce, e.g., KSCM-1, KSCM-1, KSCM-5, and KSCM-11. The modified Finkelstein reaction may be readily employed (e.g., instead of a traditional alkylation) using only NaH and a substituent alkyl group due to commercial availability of 1-(3-chloropropyl)piperidine reagent, which is less reactive than the commercially unavailable 1-(3-iodopropyl)piperidine reagent. For example, a halogen exchange is desirable for a successful reaction and 1-(3-chloropropyl)piperidine is relatively unstable and/or available only in the hydrogen chloride salt form. Thus, an additional reagent, such as the salt $K_2CO_3$, may be added to generate a free basic reagent in situ to provide a relatively cost-effective and/or efficient "one-pot" production of final carboxamide products (e.g., KSCM-1, KSCM-5, KSCM-11) in relatively good yield. Notably, purity of the compounds (e.g., KSCM-1, KSCM-5, KSCM-11) utilizing the process is very high (e.g., compared to merely using chloropropylpiperidine), which is evidenced by, e.g., nuclear magnetic resonance data, gas chromatography/mass spectroscopy data, high resolution gas chromatography/mass spectroscopy (NMR, GC/MS and HRMS) data, and so on.

A. 6-Methoxy-3-methyl-N-phenylbenzofuran-2-carboxamide (2a)

To a mixture of aniline (0.689 g, 7.4 mmol) in dichloromethane (25 mL), 3-methyl-6-methoxybenzofuran-2-carboxylic acid (1a) (1.501 g, 7.3 mmol) was added with stirring. Then DMAP (0.094 g, 0.77 mmol) was added, followed by DCC (1.583 g, 7.7 mmol). The reaction was left to stir at room temperature for 23 h. The reaction mixture was then filtered and the filtrate washed with water (20 mL×2), then 5% acetic acid (20 mL×2) and again with water (20 mL×2). The crude product was recrystallized from methanol to yield 2a as white crystals (1.37 g, 67%), mp 176-178° C.

B. 5,6-Dimethoxy-3-methyl-N-phenylbenzofuran-2-carboxamide (2b)

To a mixture of aniline (0.398 g, 4.27 mmol) in dichloromethane (15 mL), 3-methyl-5,6-dimethoxybenzofuran-2-carboxylic acid (1b) (1.005 g, 4.25 mmol) was added with stirring. Then DMAP (0.090 g, 0.44 mmol) was added, followed by DCC (0.934 g, 4.53 mmol). The reaction was left to stir at room temperature for 23 h. The reaction mixture was then filtered and the filtrate washed with water (20 mL×2), then 5% acetic acid (20 mL×2) and again with water (20 mL×2). The crude product was recrystallized from methanol to yield 2b as white crystals (0.94 g, 71%), mp 183-185° C.

C. 3-Methyl-N-phenylbenzofuran-2-carboxamide (2c)

To a mixture of aniline (0.690 g, 7.41 mmol) in dichloromethane (25 mL), 3-methylbenzofuran-2-carboxylic acid (1c) (1.00 g, 5.7 mmol) was added with stirring. Then DMAP (0.116 g, 0.57 mmol) was added, followed by DCC (1.220 g, 5.9 mmol). The reaction was left to stir at room temperature for 23 h. The reaction mixture was then filtered and the filtrate washed with water (20 mL×2), then 5% acetic acid (20 mL×2) and again with water (20 mL×2). The crude product was recrystallized from methanol to yield 2c as off-white crystals (0.896 g, 63%), mp 118-120° C.

D. 5,6-Dimethoxy-3-methyl-N-phenyl-N-(3-(piperidin-1-yl)propyl)benzofuran-2-carboxamide (KSCM-1)

Compound 2b (0.100 g, 0.321 mmol) was added to dry dichloromethane (15 mL) with stirring under nitrogen atmosphere. To this solution NaH (0.130 g, 3.25 mmol) 60% dispersion in mineral oil was added and the reaction heated at reflux for 1 h. The reaction mixture was then cooled in an ice-bath and 1-(3-chloropropyl) piperidine hydrogen chloride salt (0.110 g, 0.555 mmol), potassium carbonate (0.380 g, 2.75 mmol), tetrabutylammoniumbromide (0.046 g, 0.143 mmol) and potassium iodide (0.292 g, 1.76 mmol) added with stirring. The reaction mixture was then heated at reflux for 24 h. The reaction mixture was then cooled and slowly quenched with ethanol. The reaction mixture was washed with water (5 ml×2) and the organic layer dried over magnesium sulfate. The crude product was purified by high performance flash purification using a Biotage Isolera 4 system, SNAP ($SiO_2$) KP-NH column, solvent dichloromethane/methanol (9:1) as eluent to give 0.0841 g (60%) of KSCM-1 as a light brown paste.

E. 3-Methyl-N-phenyl-N-(3-(piperidin-1-yl)propyl)benzofuran-2-carboxamide (KSCM-5)

Compound 2c (0.200 g, 0.80 mmol) was added to dry dichloromethane (25 ml) with stirring under nitrogen atmosphere. To this solution NaH (290 mg, 7.25 mmol) 60% dispersion in mineral oil was added and at reflux for 1 h. The reaction mixture was cooled in an ice-bath and 1-(3-chloropropyl)piperidine hydrogen chloride salt (0.238 g, 1.2 mmol), potassium carbonate (0.660 g, 4.8 mmol), tetrabutylammoniumbromide (0.100 g, 0.310 mmol) and potassium iodide (0.299 g, 1.8 mmol) added with stirring. The reaction mixture was reflux for 24 h. The reaction mixture was then cooled and slowly quenched with ethanol. The reaction mixture was washed with water (10 ml×2) and the organic layer dried over magnesium sulfate. The crude product was purified by high performance flash purification using a Biotage Isolera 4 system, SNAP ($SiO_2$) KP-NH column, solvent dichloromethane/methanol (9:1) as eluent to give 0.189 g (63%) of KSCM-5 as a light brown paste.

F. 6-Methoxy-3-methyl-N-phenyl-N-(3-(piperidin-1-yl)propyl)benzofuran-2-carboxamide (KSCM-11)

Compound 2a (0.200 g, 0.71 mmol) was added to dry dichloromethane (25 mL) with stirring under nitrogen atmosphere. To this solution NaH (0.290 g, 7.25 mmol) 60% dispersion in mineral oil was added and the reaction heated at reflux for 1 h. The reaction mixture was then cooled in an ice-bath and 1-(3-chloropropyl) piperidine hydrogen chloride salt (0.238 g, 1.2 mmol), potassium carbonate (0.660 g, 4.8 mmol), tetrabutylammoniumbromide (0.090 g, 0.279 mmol) and potassium iodide (0.357 g, 2.15 mmol) added with stirring. The reaction mixture was then heated at reflux for 24 h. The reaction mixture was then cooled and slowly quenched with ethanol. The reaction mixture was washed with water (10 ml×2) and the organic layer dried over magnesium sulfate. The crude product was purified by high performance flash purification using a Biotage Isolera 4 system, SNAP ($SiO_2$) KP-NH column, solvent dichloromethane/methanol (9:1) as eluent to give 0.168 g (58%) of KSCM-11 as a brown paste.

Example Embodiment 2

Binding Assays

Radioligand binding assays using cloned G-protein coupled receptors (GPCRs), ion channels, and transporters were performed by the National Institute of Mental Health-Psychoactive Drug Screening Program (NIMH-PDSP) using membranes from transiently transfected or stable cell lines. Detailed protocols (including cell handling, buffer composition, assay conditions, etc.) for all assays are readily available. Initial primary binding screening assays were performed using a 50 µM (initial)–10 µM (final) assay concentration of reference and test compounds. The percent inhibition of specific binding by the test compound was determined and if the test compound inhibited >50% of radioligand specific binding, then secondary binding assays $K_i$ determinations were performed.

Secondary binding assays, $K_i$ determinations were performed by measuring the inhibition of radioligand binding by various concentrations of test and reference compound. In summary, compounds/ligands were prepared as a 1.0 mg/ml stock in Standard Binding Buffer (50 mM Tris HCl pH 8.0) or DMSO according to the solubility of the compound. A similar stock of haloperidol was also prepared as a reference for a positive control. Dilutions of the test and reference compounds were then prepared in Standard Binding Buffer: 0.05 nM, 0.5 nM, 1.5 nM, 5 nM, 50 nM, 150 nM, 500 nM, 1.5 µM, 5 µM and 50 µM. [$^3$H]Pentazocine (3 nM) was used as the radioligand for σ1 receptors and [$^3$H] Ditolylglguanidine (DTG) (1 nM) as the radioligand for σ2 receptors. Aliquots (50 µl) of radioligand were dispensed into the wells of a 96-well plate containing 100 µl of Standard Binding Buffer. Then, duplicate 50-µl aliquots of the test and reference compound dilutions were added. Finally, either crude membrane fractions prepared from rat brain homogenate for σ1 receptors or PC12 cell homogenates for σ2 receptors were added to the wells, and the plates shielded from light to prevent photolysis of light sensitive ligands.

For σ1 receptors, the reactions were incubated at 37° C. for 2.5 h, and for σ2 receptors, the reactions were incubated at room temperature for 2 h. Labeled receptors were harvested by rapid filtration on to Whatman GF/B glass filters pre-soaked with 0.3% polyethyleneimine using 96-well Brandel harvester. Four rapid 500 µl washes are performed with chilled Standard Binding buffer to reduce non-specific binding. Filters were placed in 6-ml scintillation tubes and allowed to dry overnight. EcoScint scintiallation cocktail (National Diagnostics) was added to each tube prior to counting. For higher throughput assays, bound radioactivity was harvested onto 0.3% polyethyleneimine-treated, 96-well filter mats using a 96 well Filtermate harvester. The filter mats were dried, the scintillate melted onto the filters and the radioactivity counted in a Microbeta scintillation counter.

Raw data (dpm) representing total radioligand binding (i.e., specific+nonspecific binding) were plotted as a function of the logarithm of the molar concentration of the competitor (i.e., test or reference compound). Non-linear regression of the normalized (i.e., percent radioligand binding compared to that observed in the absence of test or reference compound) raw data was performed in Prism 4.0 (GraphPad Software) using builtin three parameter logistic model describing ligand competition binding to radioligand-labeled sites: $y = \text{bottom} + [(\text{top}-\text{bottom})/(1+10 \times -\log IC_{50})]$ where bottom equals the residual radioligand binding measured in the presence of 10 mM reference (i.e., nonspecific binding) and top equals the total radioligand binding observed in the absence of competitor. The log $IC_{50}$ (i.e., the log of the ligand concentration that reduces radioligand binding by 50%) was thus estimated from the data and used to obtain the $K_i$ by applying the Cheng-Prusoff approximation.

Figure 1B:
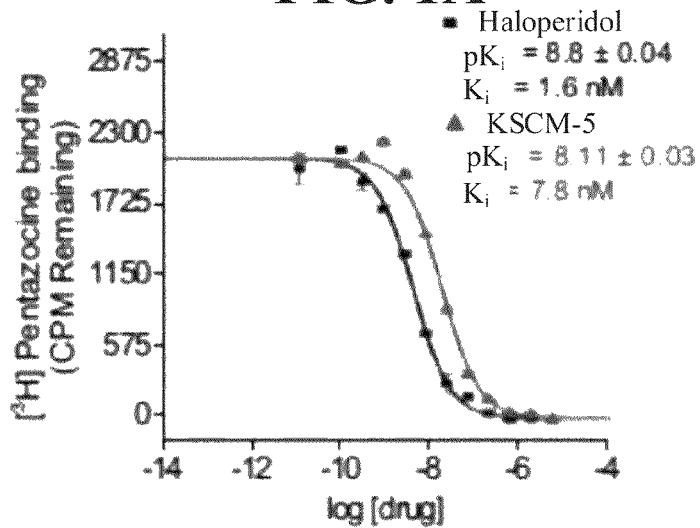
Figure 1C:
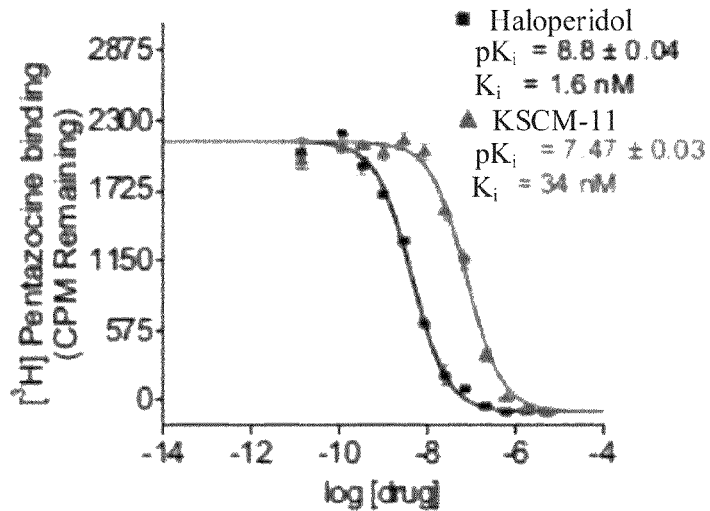
Figure 1D:
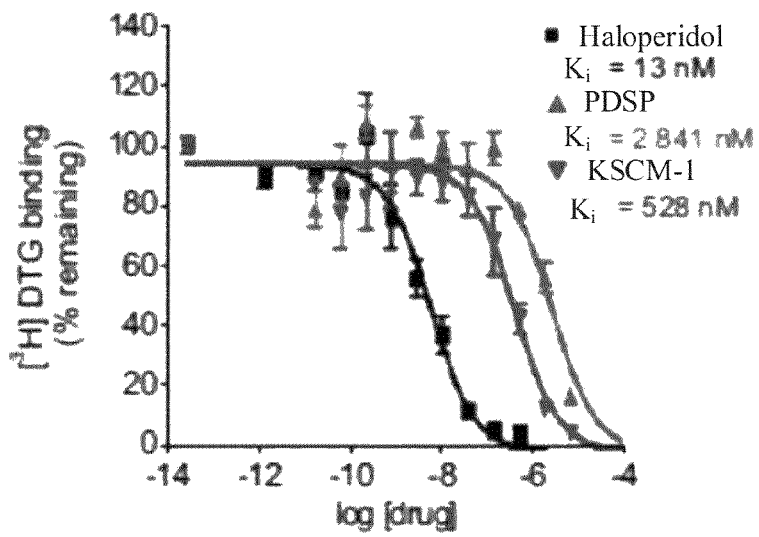
Figure 1E:
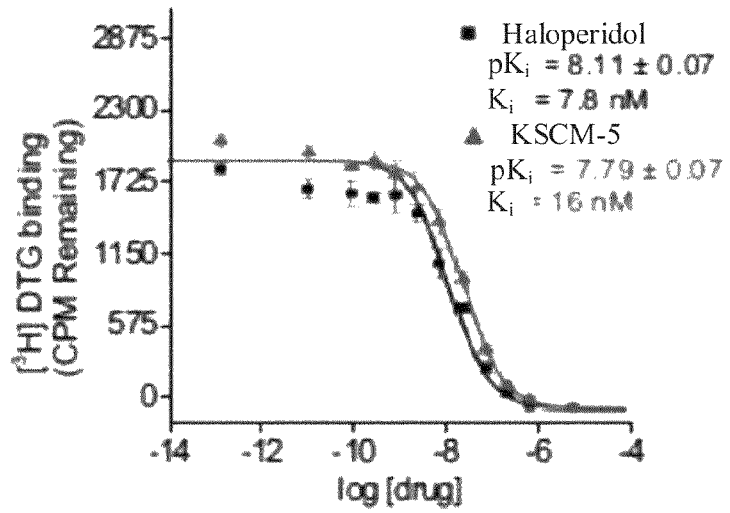
Figure 1F:
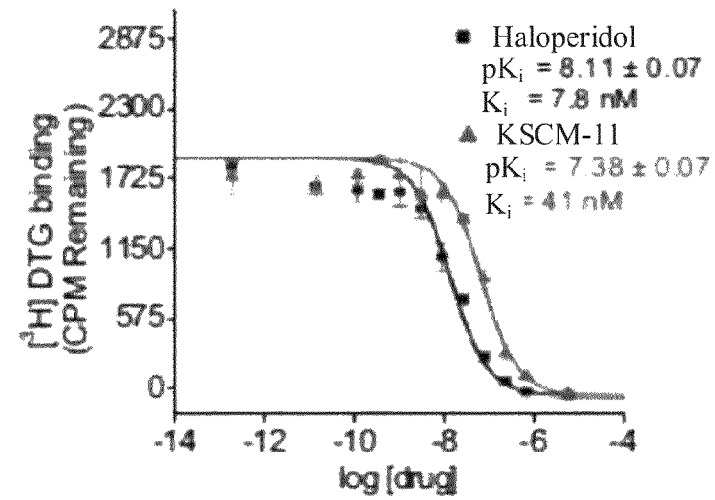

Compounds were screened by the National Institute of Mental Health-Psychoactive Drug Screening Program (NIMH-PDSP) against a panel of G-protein coupled receptors (GPCRs) and molecular targets due to the fact that many ligands with high affinity at sigma receptors have proven to also exhibit significant binding at one or more other central nervous system (CNS) relevant receptor sites. This evaluation has led to the discovery of three new sigma receptor selective ligands. Primary binding assays were performed at serotonin 5-HTs, adrenergic (Alpha1-A, -B, -D, Alpha2-A, -B, -C, Beta-1, -2, -3), cannabinoid (CB1 and CB2), Dopamine (D1-D5), histamine (H1 and H2), opioid (KOR, MOR and DOR), Muscarinic (M1-M5), N-methyl-D-aspartate (NMDA), σ1, σ2, metabotropic glutamate (mGluR5 Rat Brain), and benzodiazepine (BZP Rat Brain) receptor sites, as well as, dopamine transporter (DAT), c-aminobutyric acid type A (GABAA), norepinephrine transporter (NET) and serotonin transporter (SERT) molecular targets. Compounds showing >50% inhibition of radioligand specific binding at the stated GPCRs and molecular targets (Tables 1 and 2) were forwarded for additional screening (secondary binding assays) to determine $K_i$ values at the respective GPCR binding sites using radioligand binding assays. The σ1 receptor secondary binding curves for compounds KSCM-1, KSCM-5, KSCM-11, PDSP control, and haloperidol are shown in FIG. 1A to FIG. 1C. The σ2 receptor secondary binding curves for compounds KSCM-1, KSCM-5, KSCM-11, PDSP control, and haloperidol are shown in FIG. 1D to FIG. 1F. It was determined that compounds KSCM-1, KSCM-5 and KSCM-11 have the desired selectivity for sigma receptors (σ1 and σ2) over non-sigma receptors.

Example

TABLE 1

Primary Binding Assay at Sigma Receptors.
% Inhibition

| Compound | σ-1 | σ-2 |
|---|---|---|
| KSCM-1 | 99.8 | 81.4 |
| KSCM-5 | 100.6 | 93.5 |
| KSCM-11 | 97.7 | 88.5 |

Example

TABLE 2

Primary Binging Assay at Non-Sigma Receptors.
% Inhibition

| Compound | 5-HT2A | 5-HT2B | 5HT3 | Alpha2A | Alpha2C | D3 | M4 |
|---|---|---|---|---|---|---|---|
| KSCM-1 | 76.6 | 43.8 | 64.2 | 55.2 | 78.9 | 38.8 | 54.4 |
| KSCM-5 | 18.1 | 69.2 | 2.9 | 77.7 | 61.9 | 60.6 | 43.1 |
| KSCM-11 | 61.2 | 93.9 | 7.3 | 81.1 | 49.0 | 40.6 | 68.4 |

Secondary binding assays of these compounds showed greater affinity at sigma receptors over non-sigma receptors such as 5-HT2A, 5-HT2B, 5HT3, Alpha2A, Alpha2C, D3, and M4 (Tables 3 and 4). Consistent with documented σ1 receptor ligands, the molecular structures of KSCM-1, KSCM-5 and KSCM-11 include a basic alkyl amine group, flanked by two hydrophobic residues (an aromatic phenyl and benzofuran ring).

Example

TABLE 3

Secondary Binding Assay, $K_i$, Determination at Sigma Receptors.

| Compound | σ-1 ($K_i$, nM) | σ-2 ($K_i$, nM) | σ-2/σ-1 |
|---|---|---|---|
| KSCM-1 | 27.5 | 528 | 19 |
| KSCM-5 | 7.8 | 16 | 2 |
| KSCM-11 | 34 | 41 | 1.2 |
| Haloperidol | 1.7 | 13 | 8 |

Example

TABLE 4

Secondary Binding Assay, $K_i$ Determination at Non-Sigma Receptors.
$K_i$ (nM)

| Compound | 5-HT2A | 5-HT2B | 5HT3 | Alpha2A | Alpha2C | D3 | M4 |
|---|---|---|---|---|---|---|---|
| KSCM-1 | 2,564 | NT | 7,612 | 945 | 1,542 | NT | 2871 |
| KSCM-5 | NT | 936 | NT | 1232 | 249 | 6,739 | NT |
| KSCM-11 | 2,766 | 204 | NT | 653 | NT | NT | >10,000 |

Based upon the σ1 receptor selective ligand pharmacophore profile, a σ1 selective ligand usually possesses a primary and secondary hydrophobic site separated by an amine. The σ1 receptor site displays some bulk tolerance and so this prompted us to explore introducing a benzofuran moiety. Three example compounds have an N-arylated benzofuran-2-carboxamide scaffold which was then N-alkylated yielding N-(3-(piperidin-1-yl)propyl introducing a basic protonatable nitrogen as well as a three-carbon alkyl linker Additionally, the benzofuran molecular structure was varied by substitutions at C-5 and C-6 with methyl ether ($R_1$ and $R_2$) to explore the impact that introduction of additional hydrogen bond acceptor (HBA) centers would have on receptor binding affinity and selectivity.

The inclusion of methoxy substituents at both C-5 and C-6 of the benzofuran moiety resulted in both high affinity and selectivity at the σ1 receptor over the sigma-2 receptor as observed for KSCM-1 with $K_i$=27.5 nM at σ1 and 528 nM at σ2 (19-fold selectivity for σ1 over σ2, Table 3). KSCM-1 showed no significant affinity at non-sigma receptors selected for secondary binding assay, $K_i$ determination (Table 4), with $K_i$ values ranging from 945 nM at Alpha2A to 7,612 nM at 5-HT3. The exclusion of a methoxy substituent at C-5 of the benzofuran moiety to produce KSCM-11 resulted in a slightly decreased affinity at σ1 ($K_i$=34 nM, Table 3), however, a significant increase in affinity at σ2 ($K_i$=41 nM, Table 3) in comparison to KSCM-1. The monomethoxy compound KSCM-11 has similar affinity at both sigma receptor binding sites and thus no significant selectivity of σ1 over σ2 was observed ($K_i$=34 nM at σ1 and 41 nM at σ2, Table 3). KSCM-11 showed no significant affinity at non-sigma receptors selected for secondary binding assay, $K_i$ determination (Table 4), with $K_i$ values ranging from 204 nM at 5-HT2B to >10,000 nM at M4.

The exclusion of both methoxy substituents at C-5 and C-6 of the benzofuran moiety to produce KSCM-5 resulted in a significantly increased affinity at both σ1 ($K_i$=7.8 nM, Table 3) and σ2 ($K_i$=16 nM, Table 3) in comparison to KSCM-1 and KSCM-11. However, selectivity of KSCM-5 for σ1 over the σ2 was only twofold. KSCM-5 showed no significant affinity at non-sigma receptors selected for secondary binding assay, $K_i$ determination (Table 4), with $K_i$ values ranging from 249 nM at Alpha2C to 6,739 nM at D3. The σ2 receptor binding curves illustrate the readily noticeable link between affinity at the σ2 receptor and the loss of methoxy substituents at C-5 and C-6 of the benzofuran ring. Compound KSCM-5 without methoxy substituents was found to be a potent σ2 ligand with comparable potency to haloperidol at σ2 as is readily discernible.

In brief, three example new sigma receptor selective ligands were identified based on features of the σ1 receptor binding site which consists of an amine binding site flanked on either side by hydrophobic binding pockets. All three ligands have high affinity at σ1 with $K_i$ values ranging from 7.8 to 34 nM. KSCM-1 was the most selective with $K_i$=27.5 nM at σ1 and a 19-fold selectivity for σ1 over σ2. Example ligands KSCM-1, KSCM-5 and KSCM-11 possess basic nitrogen atoms and are structurally composed of benzofuran-2-carboxamide moieties which have been N-arylated and N-alkylated to include both N-phenyl and N-(3-(piperidin-1-yl)propyl substituents. The expedited synthetic procedures employed include regioselective microwave-assisted NBS bromination as well as microwave-assisted Perkin rearrangement reactions to prepare benzofuran-2-carboxylic acids (e.g., 1a and 1b) from the corresponding 3-bromocoumarins in very high yields.

Example Embodiment 3

Cell Viability

A. Cell Culture, Isolation, and Purification of Mitochondria.

Mouse Leydig cell line (MA-10) was grown in Waymouth media containing 15% horse serum, 5% fetal bovine serum, and 1× gentamycin, which was replaced with 250 mg/ml G418 (geneticin) for VDAC1 knockdown (ΔVDAC1) MA10 cells. Cells were maintained at 37° C. in a humidified incubator under 5% $CO_2$. To isolate mitochondria, cells were removed from tissue culture plates by gentle scrapping in phosphate-buffered saline at room temperature, incubated in hypotonic buffer (10 mM HEPES, pH 7.4) for 30 to 40 min, and mitochondria were isolated following readily available procedures. The mitochondrial preparation was verified by Western blotting with the cytochrome P450 SCC enzyme (Corgen, Tapai, Taiwan) and calnexin antibodies (Santa Cruz Biotechnology, Inc., Santa Cruz, Calif.).

B. Ligand Concentration and Cell Viability Assay.

Stock solutions (1 mM) of the ligands were made in 1× phosphate buffered saline, filter-sterilized, and then further diluted up to 1 µM with serum-free medium. Cell viability was determined by the 3-[4,5-dimethylthiazol-2yl]-2,5-diphenyltetrazolium bromide assay using a commercially available kit following the manufacturer's instructions (Promega, Madison, Wis.). MA-10 cells were plated in a 96-well plate at an initial density of 4×103 cells per well for 24 h at 37° C. in 5% $CO_2$ atm. After 24 h of serum starvation, the culture media were changed to serum-free media containing 1, 5, 10, 50, and 100 nM concentration for each KSCM ligand. Next, the cells were incubated for 2 to 3 h with 0.5 mg/ml of 3-[4,5-dimethylthiazol-2yl]-2,5-diphenyltetrazolium bromide reagent and lysed with dimethyl sulfoxide, and the absorbance was measured at 550 nm (FlexStation 3; Molecular Devices, Sunnyvale, Calif.).

Figure 2A:
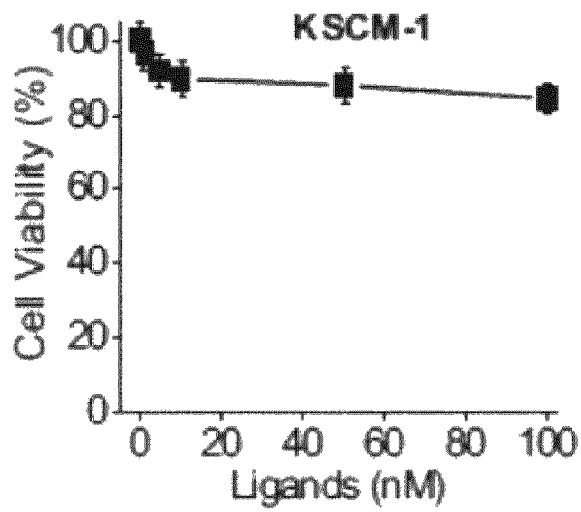
FIG. 2A to FIG. 2C are graphs of example cell viability assays after incubation for 24 h at varying concentrations of sigma receptor ligands in MA-10 cells, wherein KSCM-5 (FIG. 2B) exhibited the greatest toxicity followed by KSCM-11 (FIG. 2C) and KSCM-1 (FIG. 2A) according to an embodiment.
Figure 2B:
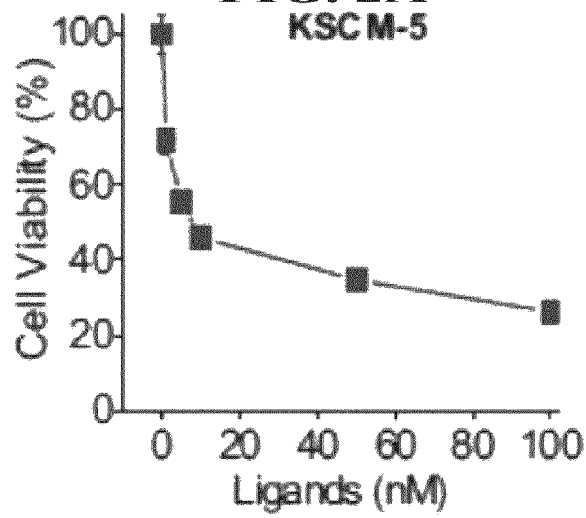
Figure 2C:
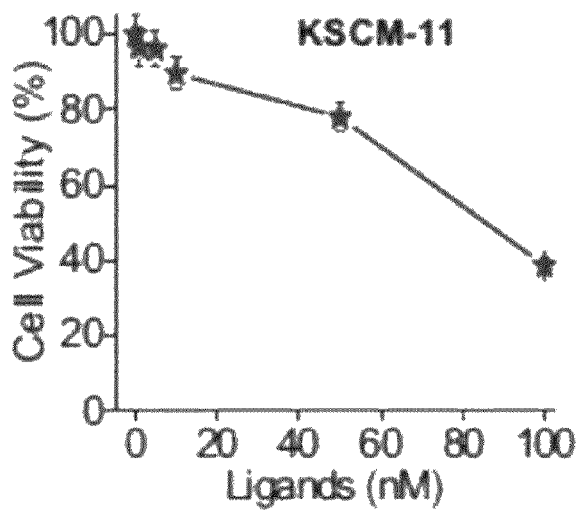

FIG. 2A to FIG. 2C shows example graphs of cell viability for the use of three example sigma receptor ligands on steroidogenic cells MA-10. Incubation with increasing concentrations of KSCM ligands decreased cell viability, although to different extents. For example, 1 nM KSCM-1 produced a 3.5% decrease in cell viability, whereas 100 nM led to a 16% decrease (FIG. 2A). In the case of KSCM-5, 1 nM decreased cell viability by 28%, whereas 100 nM resulted in a 74% decrease (FIG. 2B). Finally, like KSCM-1, KSCM-11 at lower concentrations did not greatly affect cell viability (a decrease of 3.3% with 1-5 nM); however, at 100 nM there was a σ2% decrease (FIG. 2C). It seems that KSCM-11 had a greater cytotoxic effect than KSCM-1, perhaps caused by increased affinity at the σ2 receptor. KSCM-5 produced the most potent decrease in cell viability. This compound differs from the other two ligands in that it has no methoxy groups at C-5 and C-6 of the benzofuran ring and very high affinity at both sigma receptors. A nonplanar conformation is more stable than the planar conformation because of the stronger interaction with the protein conformation and charged phospholipids, perhaps resulting in overall less toxicity.

Example Embodiment 4

Expression

A. Western Blot Analysis.

Protein (12.5 µg) was separated by 15% SDS-polyacrylamide gel electrophoresis and transferred to a polyvinylidinedifluoride membrane (Millipore Corporation, Billerica, Mass.). The membrane was blocked with 3% nonfat dry milk for 45 min, probed overnight with the primary antibodies, and then incubated with peroxide-conjugated goat anti-rabbit or anti mouse IgG (Thermo Fisher Scientific, Waltham, Mass.). Signals were developed with chemiluminescent reagent (Thermo Fisher Scientific). For loading control of all Western blots, the membrane was stained with β-actin antibody, which was previously independently stained with StAR or 3-β-hydroxysteroid dehydrogenase (3βHSD2) or VDAC1 and VDAC2 antiserum. The band intensity was determined by using Image Quant 5.2 (Phosphorimager; GE Healthcare, Chalfont St. Giles, Buckinghamshire, UK). Densitometric calculation may reflect the ratio of σ1 or VDAC2 and β-actin following an established procedure that is readily available.

B. Expression and Targeted Cytosolic Sigma Receptor.

Figure 3A:
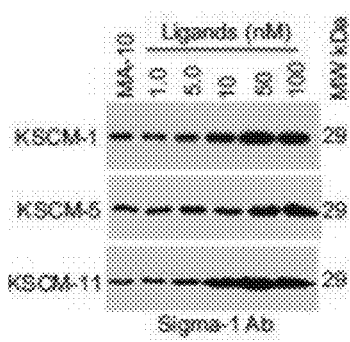
FIG. 3A to FIG. 3I are example expression data including Western blots showing that expression of the σ1 receptor increased with increasing concentrations of KSCM-1 (FIG. 3A, top), moderately increased with increasing concentrations of KSCM-11 (FIG. 3A, bottom), and remained unchanged with KSCM-5 (FIG. 3A, middle), showing the same membranes probing with β-actin corresponding to each ligand (FIG. 3B), showing the effect of incubating cells with KSCM-1, KSCM-5, and KSCM-11 on the expression of 3βHSD2 revealing no change in level of 3βHSD2 (FIG. 3C) and β-actin (FIG. 3D), showing that expression of VDAC2 increased with increasing concentrations of KSCM-1 (FIG. 3E, top) and decreased with increasing concentrations of KSCM-5 (FIG. 3E, middle) and KSCM-11 (FIG. 3E, bottom), the expression of β-actin when probed the same membranes (FIG. 3F), as well as densiometric estimations showing the effect of KSCM-1 (FIG. 3G), KSCM-5 (FIG. 3H), and KSCM-11 (FIG. 3I) on VDAC2 expression according to an embodiment.
Figure 3B:
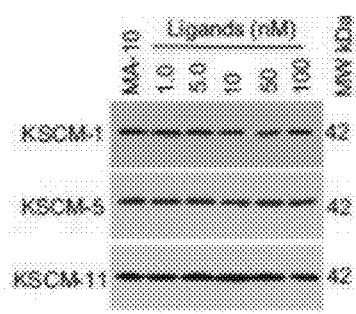
Figure 3C:
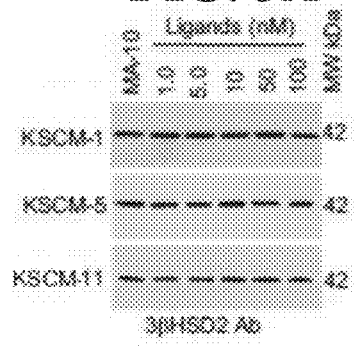
Figure 3D:
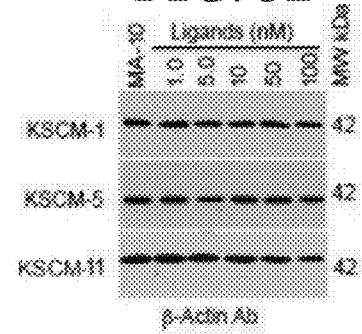
Figure 3E:
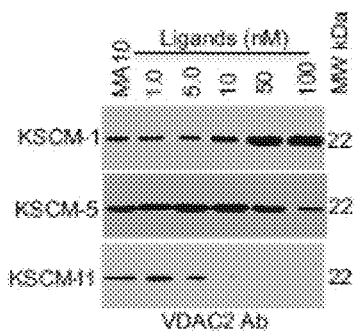
Figure 3F:
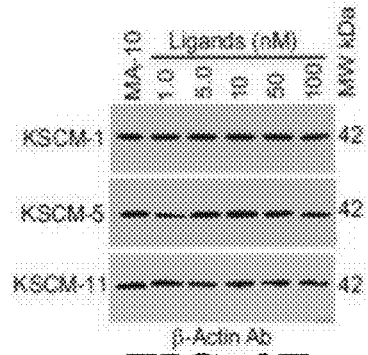
Figure 3G:
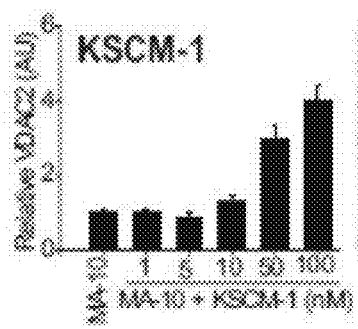
Figure 3H:
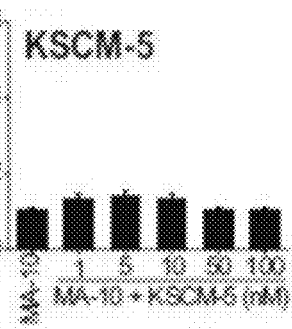
Figure 3I:
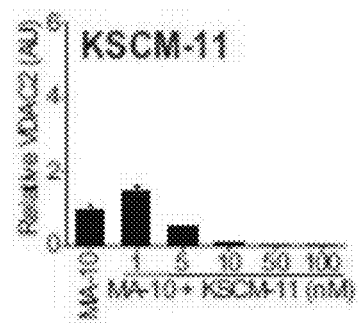

Western analysis demonstrated that incubation of MA-10 cells for 24 h with KSCM-1 and KSCM-11 increased expression of the σ1 receptor (FIG. 3A), whereas expression increased only minimally in the presence of KSCM-5 (FIG. 3A). Densitometric measurement was determined by comparing the ratio between the σ1 (FIG. 3A) and β-actin (FIG. 3B), and suggested an interaction of the ligands on the σ1 receptor (a cytosolic protein localized at the junction of the ER and mitochondria). An evaluation was made to determine whether the sigma receptor ligands had an effect on the IMM resident protein 3βHSD2, which associates with the IMM without membrane integration because of molten globule conformation. Western blotting with antibodies directed against with human 3βHSD2 and β-actin revealed no change in the levels of 3βHSD2 (FIG. 3C) and β-actin (FIG. 3D) levels at any concentrations with any of the ligands, suggesting that the KSCM series of ligands specifically targeted the cytosolic σ1 receptor. In addition, VDAC2 antibody (FIG. 3E) was used to probe and was compared with β-actin expression (FIG. 3F) of the same membrane. Densiometric estimations indicated that the expression of VDAC2 increased with increasing concentrations of KSCM-1 (FIG. 3G) and decreased with increasing concentrations of KSCM-5 (FIG. 3H) and KSCM-11 (FIG. 3I).

Example Embodiment 5

Steriodogenesis

A. Metabolic Conversion Assays and Analysis of Steroids.

To measure the conversion of [$^3$H]pregnenolone to [$^3$H] progesterone, isolated mitochondria from steroidogenic MA-10 cells (300 µg) were incubated in phosphate buffer along with the substrate, and the reaction was initiated by the NAD. For metabolic conversion of [$^{14}$C]cholesterol to pregnenolone, the reaction was initiated by the addition of NADPH, and for complete conversion we used 5-fold excess of cold carrier to reach the saturation point. The steroids were extracted with ether/acetone (9:1 v/v), and equal amounts of a cold pregnenolone-progesterone (50:50; Sigma, St. Louis, Mo.) mixture in $CH_2C_{12}$ was added as a carrier. The extracts were concentrated under a stream of nitrogen or air and then separated by thin-layer chromatography (TLC) (Whatman, Clifton, N.J.) using a chloroform/ethyl acetate (3:1) mobile phase. The spots extracted from TLC plates were subjected to gas chromatography-mass spectrometry analysis on an Agilent 7890 GC with 5975C mass spectrometer (Agilent Technologies, Santa Clara, Calif.) and analyzed.

B. Metabolic Conversion Assays and Analysis of Steroids.

Figure 4A:
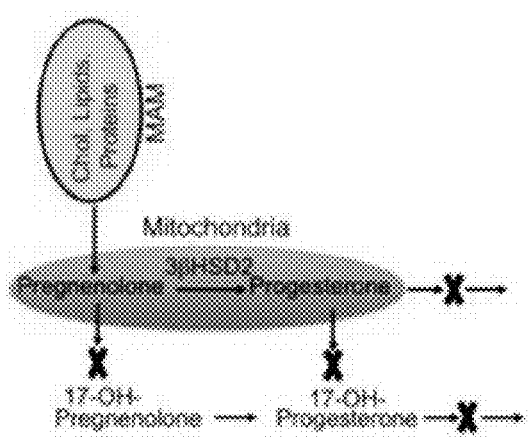
FIG. 4A to FIG. 4C are examples of lipid modulation, cholesterol conversion and/or steroidogenesis, wherein a schematic presentation of a simplified version of the steroid biosynthesis pathway and its relationship to the MAM with σ1 receptor is shown (FIG. 4A), mitochondrial metabolic conversion of [$^3$H]pregnenolone to progesterone after the addition of NAD in the presence of various concentrations of KSCM-1, KSCM-5, and KSCM-11 is shown (FIG. 4B), and quantitative estimation of metabolic conversion which shows 27% enhanced increase in activity in the presence of KSCM-1 at 10 nM (FIG. 4C) according to an embodiment.
Figure 4B:
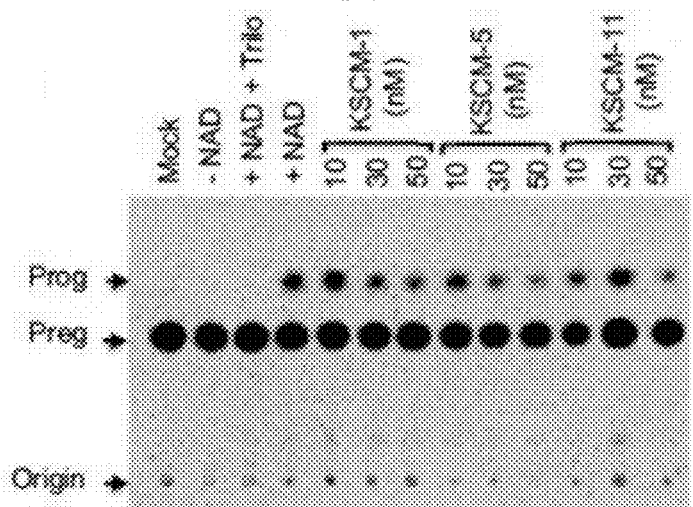
Figure 4C:
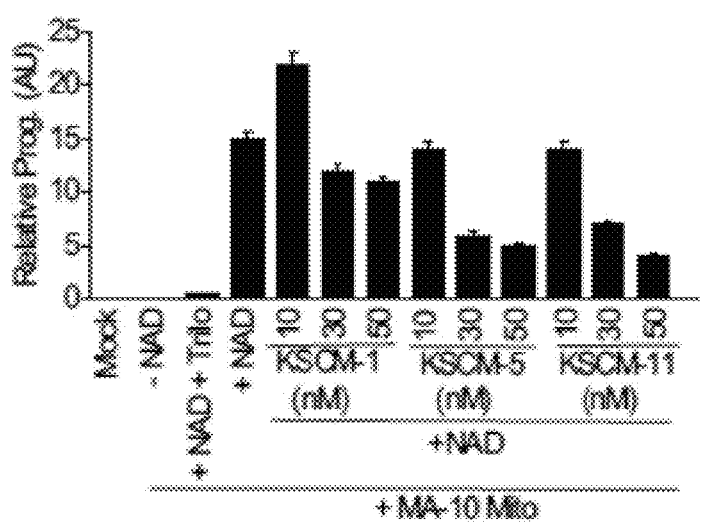

Given the potential role of σ1 in steroidogenesis (FIG. 4A), we performed conversion assays in the presence of three sigma receptor ligands. The results (FIG. 4B) showed that 10 nM KSCM-1 increased progesterone conversion more than 25% (FIG. 4C), but, with further increases in ligand concentration, reduced conversion to the basal level seen without KSCM-1. At 10 nM KSCM-5 and KSCM-11 had no effect, but conversion decreased significantly at higher concentrations. The possibility exists that the σ1 receptor transiently interacts with the OMM-associated porins. As such, the increased levels of σ1 receptor with KSCM-11 may enhance the transport of substrate cholesterol into the mitochondria, thereby increasing progesterone synthesis. The reduced metabolic activity seen with KSCM-5 and KSCM-11 may possibly be caused by an alteration in cholesterol import or an unknown mechanism.

C. Associations of Sigma Receptor with StAR and VDAC2.

Figure 5A:
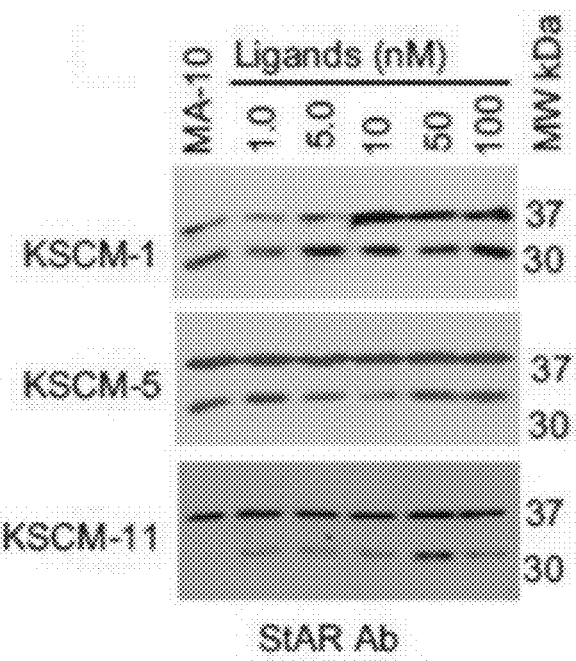
FIG. 5A to FIG. 5B are example Western blots showing the unchanged expression of mitochondrial unimported 37-kDa and imported 30-kDa StAR after incubation with KSCM-1, KSCM-5, and KSCM-11, wherein KSCM-1, at or above 10 nM, stabilizes the expression of unimported StAR, while imported 30-kDa StAR expression is unaffected (FIG. 5A), and coimmunoprecipitation of the MA-10 mitochondria with antibodies followed by Western blotting with σ1 antibody (FIG. 5B, top) and StAR antibody (FIG. 5B, middle), wherein the interaction of StAR with σ1 is shown, and wherein Western blotting of the same coimmunoprecipitation samples with IMM resident protein Tim23 (FIG. 5B, bottom) antibody showed that Tim23 that was present in MA-10 cells and pig adrenals and did not interact with other proteins according to an embodiment.
Figure 5B:
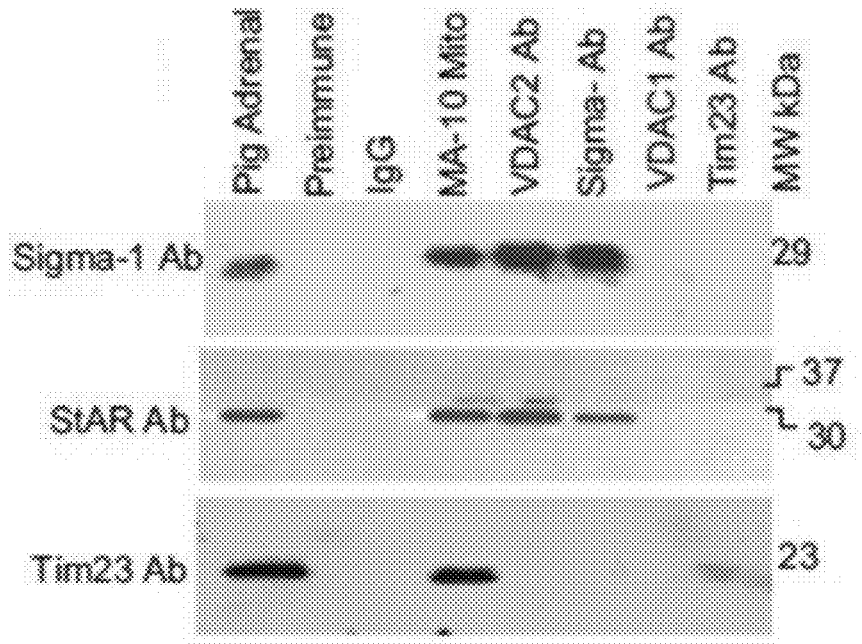

The role of KSCM ligands on the expression of StAR in MA-10 cells was evaluated. In all the cases studied, both the 37-kDa unimported and the 30-kDa mitochondrial-imported, mature protein, were observed but not the 32-kDa transient intermediate protein. The same membrane was probed first with StAR antibody and then with β-actin antibody independently. KSCM-1, but not KSCM-5 or KSCM-11, increased (and/or stabilized) the expression of unimported 37-kDa StAR (FIG. 5A). Coimmunoprecipitation experiments were performed to determine whether there was a direct interaction between σ1 receptor and StAR or VDAC2. Coimmunoprecipitation of the digitonin lysate from the mitochondria isolated from MA-10 cells showed that VDAC2 and σ1 antibodies pulled down the σ1 receptor (FIG. 5B, top). StAR is a 37-kDa protein and thus it is higher than the 28-kDa σ1 (FIG. 5A), confirming that StAR interaction with the σ1 receptor. Probing the same membrane with the Tim23 antibody failed to show any interaction with the StAR or the σ1 receptor (FIG. 5B, bottom), suggesting that the StAR interaction occurred before import into the mitochondria. Similar Western blotting of the flow-through from the previously mentioned coimmunoprecipitation experiments with σ1 antibody showed minimal intensity when pulled down with VDAC2, which suggests that the maximal interaction may be between σ1 and VDAC2 (FIG. 5B).

Because StAR is expressed on hormonal stimulation in the adrenal and gonads, StAR may act as a bridge between σ1 and VDAC2 for cholesterol loading onto the OMM. Because a specific region of MAM anchors to the OMM, where the σ1 receptor may play a role for maintaining connectivity, VDAC2 may play a greater role than VDAC1 in mediating this connection. Because VDAC2 is expressed mostly with the presence of σ1 receptor binding ligand KSCM-1, deletion of σ1 receptor may disrupt the bridge formed by VDAC2, resulting in an inhibition of cholesterol influx into the mitochondria.

Additional Notes and Examples

Example 1 may include a compound of Formula I and/or a composition including the compound of Formula 1 and a pharmaceutically acceptable carrier, wherein $R_1$ and $R_2$ are independently selected from $C_{1-20}$-alkyl, $C_{1-20}$-alkoxy, and hydrogen, $R_3$ is independently selected from (piperidin-1yl) $C_{1-20}$-alkyl, and $R_4$ is independently selected from $C_{1-20}$-alkyl, a functional group, and hydrogen.

Example 2 may include the subject matter of Example 1 and further optionally may include one or more of a salt, a prodrug, and an isomer of the compound of Formula I.

Example 3 may include the subject matter of any of Example 1 to Example 2 and further optionally may include wherein $R_1$ and $R_2$ are in one of ortho substitution, meta substitution, and para substitution.

Example 4 may include the subject matter of any of Example 1 to Example 3 and further optionally may include wherein $R_1$ and $R_2$ are independently selected from $C_{1-2}$-alkyl, $C_{1-2}$-alkoxy, and hydrogen, R3 is independently selected from (piperidin-1yl)$C_{1-5}$-alkyl, and $R_4$ is independently selected from $C_{1-2}$-alkyl, a formyl group, a carboxyl group, and hydrogen.

Example 5 may include the subject matter of any of Example 1 to Example 4 and further optionally may include wherein the compound is 5,6-dimethoxy-3-methyl-N-phenyl-N-(3-(piperidin-1-yl)propyl)benzofuran-2-carboxamide.

Example 6 may include the subject matter of any of Example 1 to Example 5 and further optionally may include wherein the compound is 3-methyl-N-phenyl-N-(3-(piperidin-1-yl)propyl)benzofuran-2-carboxamide.

Example 7 may include the subject matter of any of Example 1 to Example 6 and further optionally may include wherein the compound is 6-methoxy-3-methyl-N-phenyl-N-(3-(piperidin-1-yl) propyl)benzofuran-2-carboxamide.

Example 8 may include the subject matter of any of Example 1 to Example 7 and further optionally may include wherein the pharmaceutically acceptable carrier includes one or more of an emulsion, a paste, a cream, a lotion, a gel, jelly, ointment, oil, aerosol, powder, and solvent.

Example 9 may include the subject matter of any of Example 1 to Example 8 and further optionally may include wherein the pharmaceutically acceptable carrier includes one or more of a liposome, a micelle, a peptide, a synthetic polymer, and a natural polymer.

Example 10 may include the subject matter of any of Example 1 to Example 9 and further optionally may include wherein the pharmaceutically acceptable carrier includes a nanomaterial.

Example 11 may include the subject matter of any of Example 1 to Example 10 and further optionally may include wherein the compound of Formula I is one or more of linked with the pharmaceutically acceptable carrier and physically sequestered by the pharmaceutically acceptable carrier.

Example 12 may include the subject matter of any of Example 1 to Example 11 and further optionally may include wherein one or more of the compound of Formula I and the pharmaceutically acceptable carrier are functionalized with a ligand for a specific target.

Example 13 may include the subject matter of any of Example 1 to Example 12 and further optionally may include at least one other therapeutic compound including one or more of a neurological disease drug and a cancer drug.

Example 14 may include a kit comprising a container and one or more of a compound of Formula I and a pharmaceutically acceptable carrier. For example, the kit may include a container and the subject matter of any of Example 1 to Example 13.

Example 15 may include the subject matter of Example 14 and further optionally may include one or more of an instruction and information regarding at least the compound of Formula I.

Example 16 may include a method of using the compound of Formula I including administering the compound of Formula I to a subject having a sigma receptor to allow the compound of Formula I to bind to the sigma receptor.

Example 17 may include the subject matter of Example 16 and further optionally may include wherein the sigma receptor includes one or more of a σ1 receptor and a σ2 receptor.

Example 18 may include the subject matter of any of Example 16 to Example 17 and further optionally may include wherein the compound of Formula 1 binds to one or more of the σ1 receptor and the σ2 receptor with relatively high affinity and/or selectivity.

Example 19 may include the subject matter of any of Example 16 to Example 18 and further optionally may include identifying that the subject includes the sigma receptor and administering the compound of Formula I in response to the identification.

Example 20 may include the subject matter of any of Example 16 to Example 19 and further optionally may include administering the compound of Formula I to one or more of modulate lipid metabolism, relatively increase the expression of the σ1 receptor, relatively increase steroid hormone synthesis, relatively increase cholesterol metabolism and/or conversion, relatively increase the expression of StAR (and/or stabilize its expression), relatively increase an association between the σ1 receptor and VDAC2, and relatively decrease the number of cells overexpressing the σ2 receptor.

Example 21 may include the subject matter of any of Example 16 to Example 20 and further optionally may include wherein the compound of Formula I is administered to relatively increase the conversion of cholesterol to pregnenolone.

Example 22 may include the subject matter of any of Example 16 to Example 21 and further optionally may include wherein the compound of Formula I is administered to relatively increase the synthesis of progesterone.

Example 23 may include the subject matter of any of Example 16 to Example 22 and further optionally may include identifying one or more of a subject in need of one or more of modulation of lipid metabolism, relative increase of expression of the σ1 receptor, steroid hormone synthesis, cholesterol metabolism and/or conversion, the expression of StAR (and/or stabilize its expression), and an association between the σ1 receptor and VDAC2, a subject in need of relative decrease of the number of cells overexpressing the σ2 receptor, and a susceptible subject, and administering the compound of Formula I in response to the identification.

Example 24 may include the subject matter of any of Example 16 to Example 23 and further optionally may include wherein the subject includes one or more of a hormone deficiency patient, an Alzheimer's patient, a Parkinson's patient, a Multiple Sclerosis patient, a dementia patient, a schizophrenia patient, an amnesia patient, a cancer patient, an addiction patient, a stroke patient, and a cellular oxidative stress patient.

Example 25 may include the subject matter of any of Example 16 to Example 24 and further optionally may include administering the compound of Formula I to one or more of alleviate a symptom of a disease and reduce a relative severity and/or likelihood of a disease.

Example 26 may include the subject matter of any of Example 16 to Example 25 and further optionally may include wherein the disease includes one or more of an endocrine disease, a neurological disease, and cancer.

Example 27 may include the subject matter of any of Example 16 to Example 26 and further optionally may include wherein the endocrine disease includes a steroid hormone deficiency.

Example 28 may include the subject matter of any of Example 16 to Example 27 and further optionally may include wherein the neurological disease includes one or more of Alzheimer's disease, Parkinson's disease, dementia, schizophrenia, and amnesia.

Example 29 may include the subject matter of any of Example 16 to Example 28 and further optionally may include wherein the cancer includes one or more of lung cancer drug, liver cancer, adrenal cancer, pancreatic cancer, spleen cancer, bladder cancer, breast cancer, bone cancer, ovarian carcinoma, head cancer, neck cancer, endometrial cancer, esophageal cancer, bladder cancer, cervical cancer, central nervous system cancer, germ cell tumors, and osteogenic sarcoma.

Example 30 may include the subject matter of any of Example 16 to Example 29 and further optionally may include wherein the disease includes one or more of addiction and stroke.

Example 31 may include the subject matter of any of Example 16 to Example 30 and further optionally may include wherein the disease includes cellular oxidative stress.

Example 32 may include the subject matter of any of Example 16 to Example 31 and further optionally may include wherein the subject includes one or more of a cell, a mammal, and a human.

Example 33 may include the subject matter of any of Example 16 to Example 32 and further optionally may include wherein the cell in located one or more of in vitro and in vivo.

Example 34 may include the subject matter of any of Example 16 to Example 33 and further optionally may include administering the compound of Formula I as a composition including a pharmaceutically acceptable carrier.

Example 35 may include a method of making the compound of Formula I including utilizing a microwave-assisted synthetic pathway.

Example 36 may include the subject matter of Example 35 and further optionally may include wherein $R_1$ and $R_2$ are independently selected from $C_{1-20}$-alkyl, $C_{1-20}$-alkoxy, and hydrogen, $R_3$ is independently selected from (piperidin-1yl) $C_{1-20}$-alkyl, and $R_4$ is independently selected from $C_{1-20}$-alkyl, a functional group, and hydrogen.

Example 37 may include the subject matter of any of Example 35 to Example 36 and further optionally may include using a modified Finkelstein reaction for N-alkylation of a benzofuran-2-carboxamide.

Example 38 may include the subject matter of any of Example 35 to Example 37 and further optionally may include wherein the benzofuran-2-carboxamide includes one or more of mono-methoxy-3-methy-benzofuran-2-carboxamide, di-methoxy-3-methy-benzofuran-2-carboxamide, and 3-methy-benzofuran-2-carboxamide.

Example 39 may include the subject matter of any of Example 35 to Example 38 and further optionally may include generating a free basic reagent in situ.

Example 40 may include the subject matter of any of Example 35 to Example 39 and further optionally may include converting 1-(3-chloropropyl)piperidine hydrogen chloride salt in the presence of KI, TBAB, and $K_2CO_3$ into iodopropylpiperidine in situ.

Example 41 may include the subject matter of any of Example 35 to Example 40 and further optionally may include reacting iodopropylpiperidine with anions to produce the benzofuran-2-carboxamide.

Example 42 may include the subject matter of any of Example 35 to Example 41 and further optionally may include obtaining the anions by treating a benzofuran-2-carboxamide with NaH.

Example 43 may include the subject matter of any of Example 35 to Example 42 and further optionally may include wherein the benzofuran-2-carboxamide includes one or more of mono-methoxy-3-methyl-N-phenylbenzofuran-2-carboxamide, di-methoxy-3-methyl-N-phenylbenzofuran-2-carboxamide, and 3-methyl-N-phenylbenzofuran-2-carboxamide.

Example 44 may include the subject matter of any of Example 35 to Example 43 and further optionally may include wherein the compound of Formula I includes one or more 5,6-dimethoxy-3-methyl-N-phenyl-N-(3-(piperidin-1- yl)propyl)benzofuran-2-carboxamide, 3-methyl-N-phenyl-N-(3-(piperidin-1-yl)propyl)benzofuran-2-carboxamide, and 6-methoxy-3-methyl-N-phenyl-N-(3-(piperidin-1-yl) propyl)benzofuran-2-carboxamide It should be understood that the indefinite articles "a" or "an" carry the meaning of "one or more" or "at least one". In addition, as used in this application, a list of items joined by the terms "one or more of", "at least one of" can mean any combination of the listed terms. For example, the phrases "one or more of A, B and C" and "one or more of A, B or C" can mean A; B; C; A and B; A and C; B and C; or A, B and C. Similarly, a list of terms joined by the term "and so on" can mean the list is not an exhaustive list and may be any combination of the listed terms. For example, the phrase "A, B, C, and so on" can mean A; B; C; A and B; A and C; B and C; or A, B and C.

Those skilled in the art will appreciate from the foregoing description that the broad techniques of the embodiments may be implemented in a variety of forms. Therefore, while the embodiments have been described in connection with particular examples thereof, the true scope of the embodiments should not be so limited since other modifications will become apparent to the skilled practitioner upon a study of the drawings and the specification described above and/or as follows.

We claim:

1. A composition comprising:
a pharmaceutically acceptable carrier; and
a compound, wherein the compound is one or more of 5,6-dimethoxy-3-methyl-N-phenyl-N-(3-(piperidin-1-yl)propyl)benzofuran-2-carboxamide, 3-methyl-N-phenyl-N-(3-(piperidin-1-yl)propyl)benzofuran-2-carboxamide, and 6-methoxy-3-methyl-N-phenyl-N-(3-(piperidin-1-yl) propyl)benzofuran-2-carboxamide.

2. The composition of claim 1, further including a salt of the compound.

3. The composition of claim 1, wherein the compound is 5,6-dimethoxy-3-methyl-N-phenyl-N-(3-(piperidin-1-yl) propyl)benzofuran-2-carboxamide.

4. The composition of claim 1 wherein the compound is one or more of 3-methyl-N-phenyl-N-(3-(piperidin-1-yl) propyl)benzofuran-2-carboxamide and 6-methoxy-3-methyl-N-phenyl-N-(3-(piperidin-1-yl)propyl)benzofuran-2-carboxamide.

5. The composition of claim 1, wherein the pharmaceutically acceptable carrier is in the form of an emulsion, a paste, a cream, a lotion, a gel, jelly, ointment, oil, aerosol, powder, and/or solvent.

6. The composition of claim 1, wherein the pharmaceutically acceptable carrier is in the form of a liposome, a micelle, a peptide, a synthetic polymer, and/or a natural polymer.

7. The composition of claim 1, wherein the pharmaceutically acceptable carrier is in the form of a nanomaterial.

8. The composition of claim 1, wherein the compound is one or more of linked with the pharmaceutically acceptable carrier and physically sequestered by the pharmaceutically acceptable carrier.

9. The composition of claim 1, wherein one or more of the compound and the pharmaceutically acceptable carrier are functionalized with a ligand for a specific target.

10. The composition of claim 1, further including at least one other therapeutic compound including one or more of a neurological disease drug and a cancer drug.

11. A kit comprising:
a container; and
a composition including a pharmaceutically acceptable carrier and a compound, wherein the compound is one or more of 5,6-dimethoxy-3-methyl-N-phenyl-N-(3-(piperidin-1-yl)propyl)benzofuran-2-carboxamide, 3-methyl-N-phenyl-N-(3-(piperidin-1-yl)propyl) benzofuran-2-carboxamide, and 6-methoxy-3-methyl-N-phenyl-N-(3-(piperidin-1-yl)propyl) benzofuran-2-carboxamide.

12. The kit of claim 11, further including a salt of the compound.

13. The kit of claim 11, wherein the pharmaceutically acceptable carrier is in the form of an emulsion, a paste, a cream, a lotion, a gel, jelly, ointment, oil, aerosol, powder, solvent, a liposome, a micelle, a peptide, a synthetic polymer, a natural polymer, and/or a nanomaterial.

14. The kit of claim 11, wherein the compound is one or more of linked with the pharmaceutically acceptable carrier and physically sequestered by the pharmaceutically acceptable carrier, and wherein one or more of the compound and the pharmaceutically acceptable carrier are functionalized with a ligand for a specific target.

15. The kit of claim 11, further including one or more of an instruction and information regarding at least the compound.

16. The kit of claim 11, wherein the compound is 5,6-dimethoxy-3-methyl-N-phenyl-N-(3-(piperidin-1-yl)propyl)benzofuran-2-carboxamide.

17. The kit of claim 11, wherein the compound is one or more of 3-methyl-N-phenyl-N-(3-(piperidin-1-yl)propyl) benzofuran-2-carboxamide and 6-methoxy-3-methyl-N-phenyl-N-(3-(piperidin-1-yl)propyl)benzofuran-2-carboxamide.

* * * * *